United States Patent
Satou

(10) Patent No.: US 9,927,390 B2
(45) Date of Patent: Mar. 27, 2018

(54) GAS SENSOR ELEMENT, ITS MANUFACTURING METHOD AND GAS SENSOR INCLUDING THE GAS SENSOR ELEMENT

(71) Applicant: DENSO CORPORATION, Kariya, Aichi-pref. (JP)

(72) Inventor: Motoaki Satou, Anjo (JP)

(73) Assignee: DENSO CORPORATION, Kariya (JP)

( * ) Notice: Subject to any disclaimer, the term of this patent is extended or adjusted under 35 U.S.C. 154(b) by 357 days.

(21) Appl. No.: 14/638,400

(22) Filed: Mar. 4, 2015

(65) Prior Publication Data
US 2015/0253282 A1    Sep. 10, 2015

(30) Foreign Application Priority Data

Mar. 4, 2014    (JP) .................................. 2014-041565

(51) Int. Cl.
*G01N 27/407*    (2006.01)

(52) U.S. Cl.
CPC ..... *G01N 27/4077* (2013.01); *G01N 27/4071* (2013.01); *G01N 27/4075* (2013.01); *G01N 27/4076* (2013.01)

(58) Field of Classification Search
None
See application file for complete search history.

(56) References Cited

U.S. PATENT DOCUMENTS

| 5,948,225 A | 9/1999 | Katafuchi et al. |
| 6,254,926 B1 | 7/2001 | Katafuchi et al. |
| 6,344,118 B1 | 2/2002 | Kobayashi et al. |
| 6,354,134 B1 | 3/2002 | Katafuchi et al. |

FOREIGN PATENT DOCUMENTS

| JP | 9-2274 | 1/1997 |
| JP | 9-145669 | 6/1997 |
| JP | 9-304334 | 11/1997 |
| JP | H10-206377 | 8/1998 |
| JP | 11-51899 | 2/1999 |
| JP | 2000-81411 | 3/2000 |
| JP | 2003-287516 | 10/2003 |
| JP | 2003-322631 | 11/2003 |

*Primary Examiner* — Luan V Van
*Assistant Examiner* — Steven E Rosenwald
(74) *Attorney, Agent, or Firm* — Nixon & Vanderhye P.C.

(57) ABSTRACT

A gas sensor element includes a cup-shaped solid electrolyte body having closed and open ends, a reference electrode provided on an inner surface of the solid electrolyte body, and a measurement electrode provided on an outer surface of the solid electrolyte body. The reference electrode has a detection portion located closer to the closed end than to the open end of the solid electrolyte body, a terminal portion located closer to the open end than to the closed end of the solid electrode body, and a lead portion connecting the detection and terminal portions. Moreover, the reference electrode has a first thickness in a large-thickness region and a second thickness smaller than the first thickness in a small-thickness region. The large-thickness region includes at least part of the detection portion of the reference electrode, and the small-thickness region includes at least the lead and terminal portions of the reference electrode.

14 Claims, 17 Drawing Sheets

COMPLEX IMPEDANCE Z
FIG.4B
CONVENTIONAL
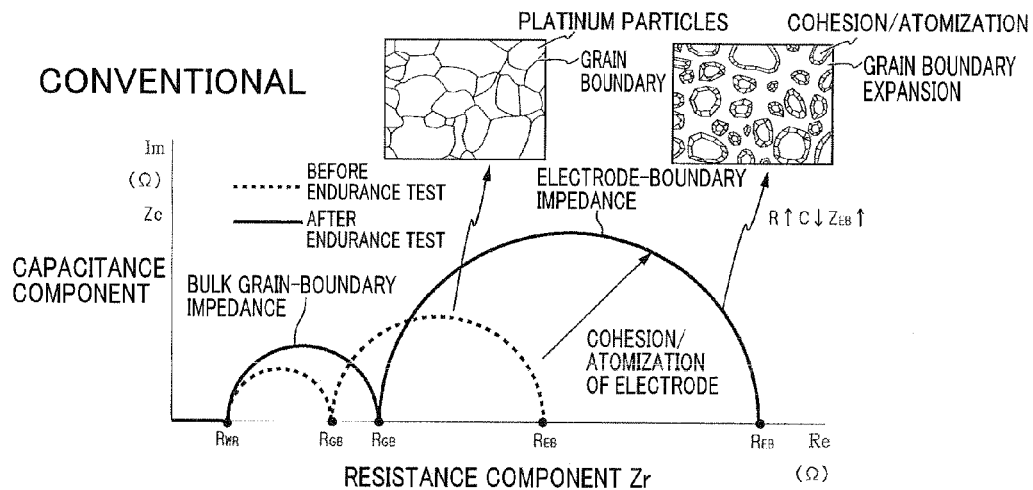
1ST EMBODIMENT

FIG. 5B

| | LARGE-THICKNESS REGION L11(mm) | DETECTION PORTION L10(mm) | LARGE-THICKNESS REGION T11(μm) | SMALL-THICKNESS REGION T12(μm) | LEAD PORTION W(mm) | REFERENCE ELECTRODE | AXIAL POSITION AND REFERENCE ELECTRODE THICKNESS | | | | | | | | | | | | | |
|---|---|---|---|---|---|---|---|---|---|---|---|---|---|---|---|---|---|---|---|---|
| | | | | | | | 0 | 2 | 3 | 5 | 6 | 7 | 10 | 15 | 20 | 25 | 30 | 35 | 40 | 44 |
| LEVEL 1 | 44 | 10 | 1.8 | 1.8 | 1.0 | | 1.8 | 1.8 | 1.8 | 1.8 | 1.8 | 1.8 | 1.8 | 1.8 | 1.8 | 1.8 | 1.8 | 1.8 | 1.8 | 1.8 |
| LEVEL 2 | 44 | 10 | 1.4 | 1.4 | 1.0 | 44mm-1.0μ | 1.4 | 1.4 | 1.4 | 1.4 | 1.4 | 1.4 | 1.4 | 1.4 | 1.4 | 1.4 | 1.4 | 1.4 | 1.4 | 1.4 |
| LEVEL 3 | 44 | 10 | 1.0 | 1.0 | 1.0 | 20mm-1.0μ | 1 | 1 | 1 | 1 | 1 | 1 | 1 | 1 | 1 | 1 | 1 | 1 | 1 | 1 |
| LEVEL 4 | 20 | 10 | 1.0 | 0.8 | 1.0 | 20mm-0.8μ | 0.8 | 0.8 | 0.8 | 0.8 | 0.8 | 0.8 | 0.8 | 0.8 | 0.8 | 0.8 | 0.8 | 0.8 | 0.8 | 0.8 |
| LEVEL 5 | 20 | 10 | 0.8 | 0.6 | 1.0 | 20mm-0.7μ | 0.7 | 0.7 | 0.7 | 0.7 | 0.7 | 0.7 | 0.7 | 0.7 | 0.7 | 0.7 | 0.6 | 0.6 | 0.6 | 0.6 |
| LEVEL 6 | 20 | 10 | 0.7 | 0.6 | 1.0 | 20mm-0.6μ | 0.6 | 0.6 | 0.6 | 0.6 | 0.6 | 0.6 | 0.6 | 0.6 | 0.6 | 0.6 | 0.6 | 0.6 | 0.6 | 0.6 |
| LEVEL 7 | 20 | 10 | 0.6 | 0.5 | 1.0 | 20mm-0.5μ | 0.5 | 0.5 | 0.5 | 0.5 | 0.5 | 0.5 | 0.5 | 0.5 | 0.5 | 0.5 | 0.5 | 0.5 | 0.5 | 0.5 |
| LEVEL 8 | 20 | 10 | 0.5 | 0.4 | 1.0 | 20mm-0.4μ | 0.4 | 0.4 | 0.4 | 0.4 | 0.4 | 0.4 | 0.4 | 0.4 | 0.4 | 0.4 | 0.4 | 0.4 | 0.4 | 0.4 |
| LEVEL 9 | 20 | 10 | 0.4 | 0.3 | 1.0 | 20mm-0.6μ | 0.6 | 0.6 | 0.6 | 0.6 | 0.6 | 0.6 | 0.6 | 0.6 | 0.6 | 0.5 | 0.5 | 0.5 | 0.5 | 0.5 |
| LEVEL 10 | 20 | 10 | 0.6 | 0.5 | 1.0 | 20mm-0.6μ | 0.6 | 0.6 | 0.6 | 0.6 | 0.6 | 0.6 | 0.6 | 0.6 | 0.6 | 0.5 | 0.5 | 0.5 | 0.5 | 0.5 |
| LEVEL 11 | 20 | 10 | 0.6 | 0.5 | 1.0 | 20mm-0.6μ | 0.6 | 0.6 | 0.6 | 0.6 | 0.6 | 0.6 | 0.6 | 0.6 | 0.6 | 0.5 | 0.5 | 0.5 | 0.5 | 0.5 |
| LEVEL 12 | 20 | 10 | 0.6 | 0.5 | 1.0 | 15mm-1.0μ | 0.6 | 0.6 | 0.6 | 0.6 | 0.6 | 0.6 | 0.6 | 1 | 0.5 | 0.5 | 0.5 | 0.5 | 0.5 | 0.5 |
| LEVEL 13 | 15 | 10 | 1.0 | 0.6 | 1.0 | 10mm-1.0μ | 1 | 1 | 1 | 1 | 1 | 1 | 1 | 0.5 | 0.5 | 0.5 | 0.5 | 0.5 | 0.5 | 0.5 |
| LEVEL 14 | 10 | 10 | 0.6 | 0.6 | 1.0 | 6mm-1.0μ | 1 | 1 | 1 | 1 | 1 | 1 | 0.5 | 0.5 | 0.5 | 0.5 | 0.5 | 0.5 | 0.5 | 0.5 |
| LEVEL 15 | 6 | 10 | 0.6 | 0.6 | 1.0 | 5mm-1.0μ | 1 | 1 | 1 | 1 | 1 | 0.5 | 0.5 | 0.5 | 0.5 | 0.5 | 0.5 | 0.5 | 0.5 | 0.5 |
| LEVEL 16 | 5 | 10 | 0.6 | 0.6 | 1.0 | 3mm-1.0μ | 1 | 1 | 1 | 0.5 | 0.5 | 0.5 | 0.5 | 0.5 | 0.5 | 0.5 | 0.5 | 0.5 | 0.5 | 0.5 |
| LEVEL 17 | 3 | 10 | 1.0 | 0.6 | 1.0 | 2mm-1.0μ | 1 | 1 | 0.5 | 0.5 | 0.5 | 0.5 | 0.5 | 0.5 | 0.5 | 0.5 | 0.5 | 0.5 | 0.5 | 0.5 |
| LEVEL 18 | 2 | 10 | 1.0 | 0.6 | 1.0 | 15mm-0.6μ | 0.6 | 0.6 | 0.6 | 0.6 | 0.6 | 0.6 | 0.6 | 0.6 | 0.5 | 0.5 | 0.5 | 0.5 | 0.5 | 0.5 |
| LEVEL 19 | 15 | 10 | 0.6 | 0.5 | 1.0 | 10mm-0.6μ | 0.6 | 0.6 | 0.6 | 0.6 | 0.6 | 0.6 | 0.6 | 0.5 | 0.5 | 0.5 | 0.5 | 0.5 | 0.5 | 0.5 |
| LEVEL 20 | 10 | 10 | 0.6 | 0.5 | 1.0 | 6mm-0.6μ | 0.6 | 0.6 | 0.6 | 0.6 | 0.6 | 0.6 | 0.5 | 0.5 | 0.5 | 0.5 | 0.5 | 0.5 | 0.5 | 0.5 |
| LEVEL 21 | 6 | 10 | 0.6 | 0.5 | 1.0 | 5mm-0.6μ | 0.6 | 0.6 | 0.6 | 0.6 | 0.6 | 0.5 | 0.5 | 0.5 | 0.5 | 0.5 | 0.5 | 0.5 | 0.5 | 0.5 |
| LEVEL 22 | 5 | 10 | 0.6 | 0.5 | 1.0 | 3mm-0.6μ | 0.6 | 0.6 | 0.6 | 0.6 | 0.6 | 0.5 | 0.5 | 0.5 | 0.5 | 0.5 | 0.5 | 0.5 | 0.5 | 0.5 |
| LEVEL 23 | 3 | 10 | 0.6 | 0.5 | 1.0 | 2mm-0.6μ | 0.6 | 0.6 | 0.6 | 0.6 | 0.5 | 0.5 | 0.5 | 0.5 | 0.5 | 0.5 | 0.5 | 0.5 | 0.5 | 0.5 |
| LEVEL 24 | 2 | 10 | 0.6 | 0.5 | 1.0 | 5mm-1.0μ | 0.6 | 0.6 | 0.6 | 0.5 | 0.5 | 0.5 | 0.5 | 0.5 | 0.5 | 0.5 | 0.5 | 0.5 | 0.5 | 0.5 |
| LEVEL 25 | 5 | 10 | 1.0 | 0.8, 0.6 | 1.0 | 5mm-0.7μ | 1 | 1 | 1 | 1 | 0.8 | 0.8 | 0.8 | 0.8 | 0.8 | 0.8 | 0.8 | 0.8 | 0.8 | 0.8 |
| LEVEL 26 | 5 | 10 | 0.7 | 0.6, 0.5 | 1.0 | 5mm-0.6μ | 0.7 | 0.7 | 0.7 | 0.7 | 0.6 | 0.6 | 0.6 | 0.6 | 0.6 | 0.6 | 0.6 | 0.6 | 0.6 | 0.6 |
| LEVEL 27 | 5 | 10 | 0.6 | 0.5 | 3.0 | 5mm-0.6μ | 0.6 | 0.6 | 0.6 | 0.6 | 0.5 | 0.5 | 0.5 | 0.5 | 0.5 | 0.5 | 0.5 | 0.5 | 0.5 | 0.5 |
| LEVEL 28 | 5 | 10 | 0.6 | 0.5 | 6.0 | 5mm-0.6μ | 0.6 | 0.6 | 0.6 | 0.6 | 0.5 | 0.5 | 0.5 | 0.5 | 0.5 | 0.5 | 0.5 | 0.5 | 0.5 | 0.5 |
| LEVEL 29 | 5 | 10 | 0.6 | 0.5 | 9.0 | 5mm-0.6μ | 0.6 | 0.6 | 0.6 | 0.6 | 0.5 | 0.5 | 0.5 | 0.5 | 0.5 | 0.5 | 0.5 | 0.5 | 0.5 | 0.5 |
| LEVEL 30 | 5 | 10 | 0.6 | 0.5 | 10.7 | 5mm-0.6μ | 0.6 | 0.6 | 0.6 | 0.6 | 0.5 | 0.5 | 0.5 | 0.5 | 0.5 | 0.5 | 0.5 | 0.5 | 0.5 | 0.5 |
| LEVEL 31 | 44 | 44 | 1.0 | 1.0 | 10.7 | 44mm-1.0μ | 1 | 1 | 1 | 1 | 1 | 1 | 1 | 1 | 1 | 1 | 1 | 1 | 1 | 1 |
| LEVEL 32 | 20 | 10 | 0.6 | 0.5 | 1.0 | 20mm-0.6μ | 0.6 | 0.6 | 0.6 | 0.6 | 0.6 | 0.6 | 0.6 | 0.6 | 0.6 | 0.5 | 0.5 | 0.5 | 0.5 | 0.5 |
| LEVEL 33 | 20 | 10 | 0.6 | 0.5 | 1.0 | 20mm-0.6μ | 0.6 | 0.6 | 0.6 | 0.6 | 0.6 | 0.6 | 0.6 | 0.6 | 0.6 | 0.5 | 0.5 | 0.5 | 0.5 | 0.5 |

FIG.5C

| | MEASUREMENT ELECTRODE | | | HEAT RESISTANCE (ELEMENT MAX950°C) | | | | | | | | | | | | EVALUATION | ELEMENT EVALUATION | | | | | | EVALUATION | CONTROLLED TEMPERATURE VARIATION |
|---|---|---|---|---|---|---|---|---|---|---|---|---|---|---|---|---|---|---|---|---|---|---|---|---|
| | LARGE-THICKNESS REGION | SMALL-THICKNESS REGION | | 600°C IMPEDANCE RESISTANCE (Ω) | | | | | | OUTPUT (V) | | | | | | | INITIAL IMPEDANCE RESISTANCE (Ω) | | | | | | | |
| L13(mm) | T13(μm) | T14(μm) | | 0 | 400 | 800 | 1200 | 1600 | | 0 | 400 | 800 | 1200 | 1600 | | HEAT RESISTANCE | TEMPERATURE (°C) | 500 | 600 | 700 | | | COST | |
| 44 | 0.8 | 0.8 | LEVEL 1 | 162 | 511 | 527 | 533 | 538 | | 0.92 | 0.92 | 0.91 | 0.91 | 0.9 | | ○ | LEVEL 1 | 644 | 162 | 24 | | ○ | × | |
| 44 | 0.8 | 0.8 | LEVEL 2 | 166 | 512 | 535 | 538 | 544 | | 0.92 | 0.92 | 0.91 | 0.91 | 0.9 | | ○ | LEVEL 2 | 648 | 166 | 27 | | ○ | △ | |
| 44 | 0.8 | 0.8 | LEVEL 3 | 170 | 520 | 540 | 545 | 550 | | 0.92 | 0.92 | 0.91 | 0.91 | 0.9 | | ○ | LEVEL 3 | 650 | 170 | 30 | | ○ | △ | |
| 44 | 0.8 | 0.8 | LEVEL 4 | 175 | 525 | 545 | 550 | 555 | | 0.91 | 0.91 | 0.91 | 0.9 | 0.9 | | ○ | LEVEL 4 | 690 | 175 | 32 | | ○ | ○ | |
| 44 | 0.8 | 0.8 | LEVEL 5 | 180 | 530 | 550 | 555 | 560 | | 0.91 | 0.91 | 0.91 | 0.9 | 0.9 | | ○ | LEVEL 5 | 730 | 180 | 34 | | ○ | ○ | |
| 44 | 0.8 | 0.8 | LEVEL 6 | 185 | 535 | 555 | 560 | 565 | | 0.91 | 0.9 | 0.9 | 0.9 | 0.9 | | ○ | LEVEL 6 | 770 | 185 | 36 | | ○ | ○ | |
| 44 | 0.8 | 0.8 | LEVEL 7 | 190 | 545 | 560 | 565 | 570 | | 0.91 | 0.92 | 0.91 | 0.91 | 0.9 | | ○ | LEVEL 7 | 800 | 190 | 38 | | ○ | ○ | |
| 44 | 0.8 | 0.8 | LEVEL 8 | 240 | 1150 | 1400 | 1450 | 1500 | | 0.91 | 0.91 | 0.9 | 0.9 | 0.89 | | × | LEVEL 8 | 1600 | 240 | 30 | | ○ | ○ | |
| 44 | 0.8 | 0.8 | LEVEL 9 | 300 | 1500 | 2200 | 2700 | 3000 | | 0.91 | 0.91 | 0.9 | 0.9 | 0.89 | | × | LEVEL 9 | 2500 | 300 | 30 | | ○ | ○ | |
| 44 | 1.4 | 1.4 | LEVEL 10 | 190 | 545 | 560 | 565 | 567 | | 0.92 | 0.92 | 0.91 | 0.9 | 0.89 | | ○ | LEVEL 10 | 795 | 190 | 37 | | ○ | ○ | |
| 44 | 1.8 | 1.8 | LEVEL 11 | 187 | 542 | 558 | 562 | 565 | | 0.91 | 0.91 | 0.91 | 0.91 | 0.89 | | ○ | LEVEL 11 | 792 | 187 | 36 | | ○ | ○ | |
| 44 | 2.2 | 2.2 | LEVEL 12 | 184 | 540 | 557 | 560 | 562 | | 0.91 | 0.92 | 0.91 | 0.91 | 0.89 | | ○ | LEVEL 12 | 785 | 184 | 35 | | ○ | × | |
| 44 | 0.8 | 0.8 | LEVEL 13 | 170 | 521 | 542 | 548 | 550 | | 0.92 | 0.92 | 0.91 | 0.91 | 0.89 | | ○ | LEVEL 13 | 650 | 170 | 30 | | ○ | ○ | |
| 44 | 0.8 | 0.8 | LEVEL 14 | 171 | 525 | 545 | 558 | 560 | | 0.92 | 0.92 | 0.91 | 0.9 | 0.89 | | ○ | LEVEL 14 | 680 | 171 | 33 | | ○ | ○ | |
| 44 | 0.8 | 0.8 | LEVEL 15 | 174 | 530 | 560 | 565 | 570 | | 0.92 | 0.92 | 0.91 | 0.9 | 0.89 | | ○ | LEVEL 15 | 710 | 174 | 36 | | ○ | ○ | |
| 44 | 0.8 | 0.8 | LEVEL 16 | 185 | 535 | 570 | 575 | 580 | | 0.91 | 0.91 | 0.9 | 0.9 | 0.82 | | ○ | LEVEL 16 | 740 | 185 | 39 | | ○ | ○ | |
| 44 | 0.8 | 0.8 | LEVEL 17 | 190 | 1170 | 1180 | 1190 | 1200 | | 0.85 | 0.86 | 0.84 | 0.83 | 0.82 | | × | LEVEL 17 | 770 | 190 | 40 | | ○ | ○ | |
| 44 | 0.8 | 0.8 | LEVEL 18 | 195 | 1470 | 1480 | 1490 | 1500 | | 0.83 | 0.82 | 0.83 | 0.83 | 0.81 | | × | LEVEL 18 | 800 | 195 | 75 | | ○ | ○ | |
| 44 | 0.8 | 0.8 | LEVEL 19 | 170 | 580 | 590 | 595 | 600 | | 0.92 | 0.92 | 0.91 | 0.9 | 0.89 | | ○ | LEVEL 19 | 655 | 180 | 32 | | ○ | ○ | |
| 44 | 0.8 | 0.8 | LEVEL 20 | 172 | 583 | 593 | 599 | 610 | | 0.92 | 0.92 | 0.91 | 0.9 | 0.89 | | ○ | LEVEL 20 | 685 | 182 | 35 | | ○ | ○ | |
| 44 | 0.8 | 0.8 | LEVEL 21 | 175 | 590 | 600 | 615 | 620 | | 0.92 | 0.92 | 0.91 | 0.9 | 0.89 | | ○ | LEVEL 21 | 715 | 185 | 38 | | ○ | ○ | |
| 44 | 0.8 | 0.8 | LEVEL 22 | 195 | 595 | 615 | 628 | 630 | | 0.91 | 0.91 | 0.9 | 0.9 | 0.89 | | ○ | LEVEL 22 | 745 | 200 | 41 | | ○ | ○ | |
| 44 | 0.8 | 0.8 | LEVEL 23 | 200 | 1260 | 1270 | 1290 | 1300 | | 0.84 | 0.84 | 0.83 | 0.82 | 0.81 | | × | LEVEL 23 | 1100 | 192 | 43 | | ○ | ○ | |
| 44 | 0.8 | 0.8 | LEVEL 24 | 215 | 1540 | 1560 | 1580 | 1600 | | 0.81 | 0.8 | 0.81 | 0.81 | 0.8 | | × | LEVEL 24 | 1700 | 195 | 45 | | ○ | ○ | |
| 44 | 0.8 | 0.8 | LEVEL 25 | 173 | 525 | 540 | 560 | 571 | | 0.92 | 0.92 | 0.91 | 0.9 | 0.89 | | ○ | LEVEL 25 | 750 | 173 | 42 | | ○ | ○ | |
| 44 | 0.8 | 0.8 | LEVEL 26 | 160 | 550 | 571 | 586 | 590 | | 0.92 | 0.92 | 0.91 | 0.9 | 0.89 | | ○ | LEVEL 26 | 760 | 160 | 43 | | ○ | ○ | |
| 44 | 0.8 | 0.8 | LEVEL 27 | 180 | 479 | 503 | 514 | 520 | | 0.92 | 0.92 | 0.91 | 0.9 | 0.89 | | ○ | LEVEL 27 | 730 | 180 | 39 | | ○ | ○ | |
| 44 | 0.8 | 0.8 | LEVEL 28 | 175 | 442 | 460 | 476 | 480 | | 0.92 | 0.92 | 0.91 | 0.9 | 0.89 | | ○ | LEVEL 28 | 727 | 175 | 35 | | ○ | ○ | |
| 44 | 0.8 | 0.8 | LEVEL 29 | 170 | 420 | 432 | 435 | 440 | | 0.92 | 0.92 | 0.91 | 0.9 | 0.89 | | ○ | LEVEL 29 | 724 | 170 | 30 | | ○ | ○ | |
| 44 | 0.8 | 0.8 | LEVEL 30 | 160 | 390 | 410 | 415 | 420 | | 0.92 | 0.92 | 0.91 | 0.9 | 0.89 | | ○ | LEVEL 30 | 720 | 160 | 25 | | ○ | ○ | |
| 44 | 0.8 | 0.8 | LEVEL 31 | 150 | 370 | 390 | 395 | 400 | | 0.92 | 0.92 | 0.91 | 0.9 | 0.89 | | ○ | LEVEL 31 | 250 | 150 | 20 | | × | × | |
| 44 | 0.7 | 0.7 | LEVEL 32 | 196 | 630 | 680 | 760 | 800 | | 0.79 | 0.79 | 0.78 | 0.78 | 0.78 | | ○ | LEVEL 32 | 950 | 196 | 43 | | ○ | ○ | |
| 44 | 0.7 | 0.6 | LEVEL 33 | 203 | 1150 | 1350 | 1600 | 1700 | | 0.8 | 0.79 | 0.78 | 0.78 | 0.78 | | × | LEVEL 33 | 1100 | 203 | 50 | | ○ | ○ | |

FIG.6
LEVELS 1 ~ 26,32,33
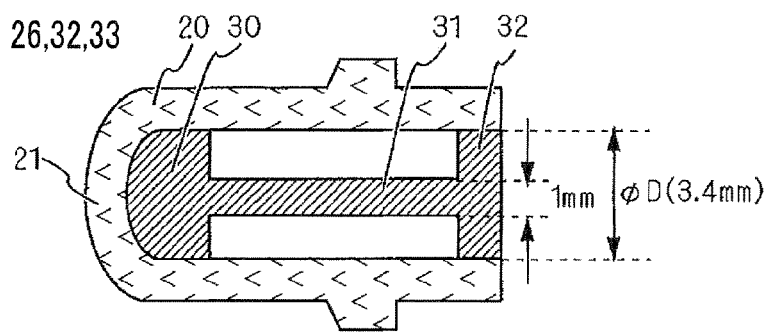
LEVELS 27 ~ 29
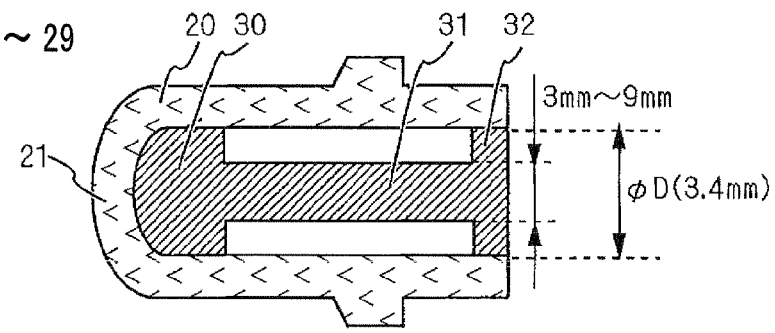
LEVELS 30,31
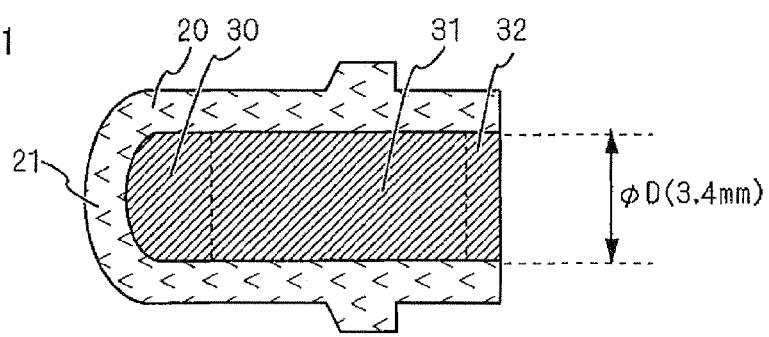

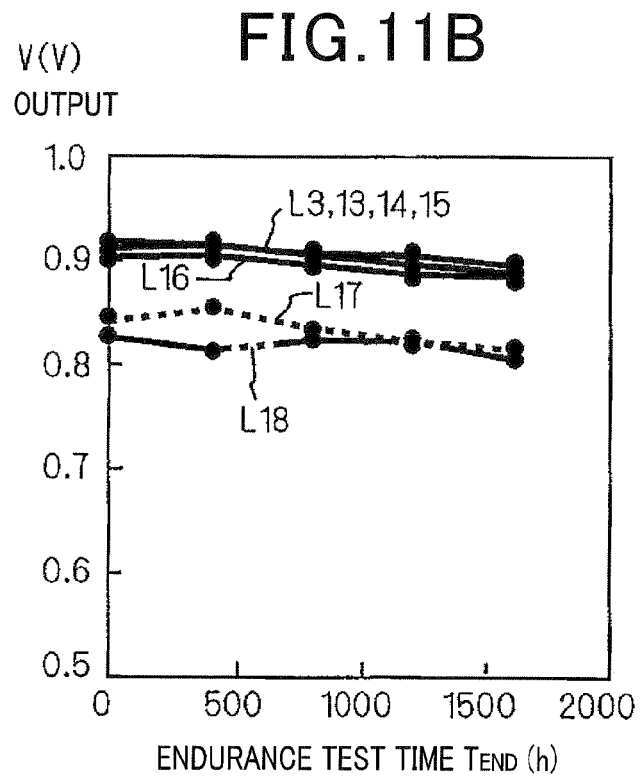
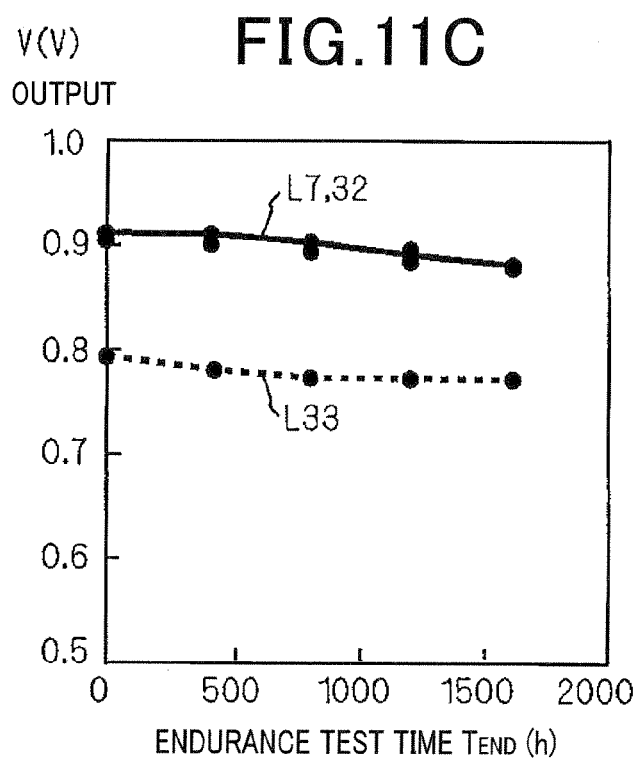

FIG.13

| ORGANIC SOLVENT | BOILING POINT [°C] | LINEWIDTH OF ACTIVE BASE MATERIAL [mm]*1 | PLATING LINEWIDTH [mm] | PLATING BLEED | DRIPPING OF ACTIVE BASE MATERIAL | EVALUATION |
|---|---|---|---|---|---|---|
| DICHLOROETHANE | 40 | 1.5 | 1.6 | NOT OBSERVED | NOT OBSERVED | ○ |
| CHLOROFORM | 61 | 1.5 | 1.6 | NOT OBSERVED | NOT OBSERVED | ○ |
| METHYL ETHYL KETONE | 80 | 1.5 | 1.7 | NOT OBSERVED | NOT OBSERVED | ○ |
| CYCLOHEXANE | 81 | 1.5 | 1.7 | NOT OBSERVED | NOT OBSERVED | ○ |
| ISOPROPYL ALCOHOL | 82 | 1.5 | 1.7 | NOT OBSERVED | NOT OBSERVED | ○ |
| ISOBUTYL ALCOHOL | 108 | 1.5 | 1.9 | NOT OBSERVED | OBSERVED | △ |
| DIPENTENE | 178 | 1.5 | 2.1 | OBSERVED | OBSERVED | × |
| TERPINEOL | 217 | 1.5 | 2.3 | OBSERVED | OBSERVED | × | ns
GAS SENSOR ELEMENT, ITS MANUFACTURING METHOD AND GAS SENSOR INCLUDING THE GAS SENSOR ELEMENT

CROSS-REFERENCE TO RELATED APPLICATION

This application is based on and claims priority from Japanese Patent Application No. 2014-41565, filed on Mar. 4, 2014, the content of which is hereby incorporated by reference in its entirety into this application.

BACKGROUND

1. Technical Field

The present invention relates to a gas sensor element for sensing the concentration of a specific component in a gas to be measured (to be simply referred to as a measurement gas hereinafter), to a method of manufacturing the gas sensor element, and to a gas sensor which includes the gas sensor element.

2. Description of Related Art

Conventionally, in the exhaust system of an internal combustion engine of a motor vehicle, there is generally arranged a gas sensor for sensing the concentration of a specific component (e.g., oxygen) in the exhaust gas from the engine. Further, based on the concentration of the specific component sensed by the gas sensor, various controls are performed which include, for example, an air/fuel ratio control and a temperature control of a catalyst used for treatment of the exhaust gas.

Moreover, the gas sensor may have a cup-shaped gas sensor element built therein. The gas sensor element includes: a solid electrolyte body that is formed of a solid electrolyte material (e.g., zirconia), which has oxygen ion conductivity, into a cup shape (or bottomed tubular shape); a measurement electrode provided on an outer surface of the solid electrolyte body so as to be exposed to the measurement gas (i.e., the exhaust gas from the engine); and a reference electrode provided on an inner surface of the solid electrolyte body so as to be exposed to a reference gas (e.g., air). Further, the gas sensor may be configured as an oxygen sensor to sense the electrical potential difference between the measurement and reference electrodes, which is caused by the difference in oxygen concentration between the measurement gas and the reference gas, and determine the concentration of oxygen in the measurement gas based on the sensed electric potential difference.

Furthermore, for ensuring prompt activation of the solid electrolyte body, the gas sensor may further have a heater built therein. The heater generates heat upon being supplied with electric power, thereby heating the gas sensor element. Further, it is possible to measure change in the complex impedance of the gas sensor element and control the temperature of the heater based on the measured change.

However, in the above case, in long-term use of the gas sensor, the measurement and reference electrodes will be repeatedly heated by the heater, causing cohesion of platinum particles that constitute the electrodes and thereby changing the grain-boundary capacitance. Consequently, the complex impedance of the gas sensor element will be increased, thereby lowering accuracy of the temperature control of the heater.

Japanese Patent Application Publication No. JP2003322631A discloses an oxygen sensor that includes a sensing element (or gas sensor element). In the sensing element, of the formation range of a reference electrode on an inner surface of the sensing element and the formation range of a measurement electrode on an outer surface of the sensing element, at least the formation range of the measurement electrode is set so as to be widest (or largest in circumferential length) at a high-temperature portion of the sensing element, where the temperature is highest in the sensing element, and to be narrowed (or reduced in circumferential length) as receding from the high-temperature portion.

More specifically, according to the disclosure of the above patent document, the formation range of the measurement electrode is set so as to be widest at a bottom portion of the sensing element and in the vicinity of the bottom portion. The bottom portion is most exposed to the exhaust gas (i.e., the measurement gas) and thus the temperature at the bottom portion is highest in the sensing element. Consequently, by setting the formation range of the measurement electrode so as to be widest at the bottom portion and in its vicinity, it is possible to secure the durability of the measurement electrode to heat. Moreover, by setting the formation range of the measurement electrode so as to be narrowed as getting away from the bottom portion, it is possible to suppress the influence of a non-activated part of the sensing element on the measurement electrode, thereby securing the responsiveness of the gas sensor.

However, the sensing element is heated by the exhaust gas over its entire circumference. Therefore, the temperature of the sensing element is constant in its circumferential direction.

Accordingly, the probability of the measurement electrode being broken at the high-temperature portion of the sensing element due to cohesion of the platinum particles is also constant in the circumferential direction. Therefore, even if the formation range of the measurement electrode is set as disclosed in the above patent document, it may be difficult to reliably improve the durability of the measurement electrode.

In addition, for the same reasons as the measurement electrode, it may also be difficult to reliably improve the durability of the reference electrode even if the formation range of the reference electrode is set as disclosed in the above patent document.

Moreover, in conventional gas sensor elements, the thickness (or film thickness) of the reference electrode is set to be constant. Consequently, upon exposure of a detection portion of the reference electrode to high temperature for a long period of time, cohesion of platinum particles may occur at the detection portion, thereby increasing the complex impedance of the gas sensor element. Accordingly, when the temperature of the heater is controlled based on the complex impedance of the gas sensor element, there may occur a deviation between a target temperature and the actual temperature of the heater. As a result, it may be impossible to stably and accurately sense the concentration of the specific component in the measurement gas.

SUMMARY

According to exemplary embodiments, there is provided a gas sensor element. The gas sensor element includes: a cup-shaped solid electrolyte body having a closed end on a distal side and an open end on a proximal side in an axial direction of the solid electrolyte body; a reference electrode provided on an inner surface of the solid electrolyte body; and a measurement electrode provided on an outer surface of the solid electrolyte body. The gas sensor element has a detection portion of a predetermined extent located closer to the closed end than to the open end of the solid electrolyte body. The detection portion of the gas sensor element is comprised of a detection portion of the measurement electrode to be exposed to a measurement gas, a detection portion of the reference electrode to be exposed to a reference gas, and a portion of the solid electrolyte body interposed between the detection portions of the measurement and reference electrodes. The measurement electrode further has a terminal portion located closer to the open end than to the closed end of the solid electrode body and a lead portion connecting the detection and terminal portions of the measurement electrode. The reference electrode further has a terminal portion located closer to the open end than to the closed end of the solid electrode body and a lead portion connecting the detection and terminal portions of the reference electrode. Moreover, the reference electrode has a first thickness in a large-thickness region and a second thickness smaller than the first thickness in a small-thickness region. The large-thickness region includes at least part of the detection portion of the reference electrode, and the small-thickness region includes at least the lead and terminal portions of the reference electrode.

With the above configuration, when the gas sensor element is heated by a heater to activate the solid electrolyte body, the temperature of the reference electrode will reach a maximum temperature in the detection portion of the reference electrode. However, by setting the large-thickness region to include at least part of the detection portion of the reference electrode, it will become difficult for cohesion of platinum particles constituting the reference electrode to occur with long-term use of the gas sensor element. Consequently, it will be possible to suppress change in the impedance of the gas sensor element with long-term use of the gas sensor element, thereby securing high accuracy of the temperature control of the heater based on the impedance. Moreover, it will also be possible to secure high durability of the reference electrode, thereby securing high responsiveness and stable output of the gas sensor element.

Furthermore, by setting the small-thickness region to include at least the lead and terminal portions of the reference electrode, it will be possible to reduce the amount of platinum used for formation of the reference electrode, thereby lowering the manufacturing cost of the gas sensor element. In addition, it will also be possible to increase the resistance of the reference electrode and thus relatively lower the influence of the capacitance component of the impedance, thereby further improving the stability of output of the gas sensor element.

Preferably, the large-thickness region includes at least a region in which when the gas sensor element is heated by the heater to activate the solid electrolyte body, the temperature of the reference electrode is within a range of 1.5% from a maximum temperature of the detection portion of the reference electrode.

It is also preferable that a proximal end of the large-thickness region is positioned in the axial direction of the solid electrolyte body within a range of 5 to 20 mm from a distal end of the inner surface of the solid electrolyte body.

The detection portion of the reference electrode may be formed over an entire circumference of the inner surface of the solid electrolyte body. The lead portion of the reference electrode may be formed in the shape of a strip extending in the axial direction of the solid electrolyte body at a constant circumferential width. The terminal portion of the reference electrode may be formed over an entire or partial circumference of the inner surface of the solid electrolyte body.

It is preferable that the first thickness of the reference electrode in the large-thickness region is larger than the second thickness of the reference electrode in the small-thickness region by 0.1 μm or more.

It is also preferable that the first thickness of the reference electrode in the large-thickness region is greater than or equal to 0.6 μm and less than or equal to 1.4 μm.

Part of the detection portion of the reference electrode may fall outside the large-thickness region. In this case, it is preferable that the part of the detection portion of the reference electrode has the second thickness which is greater than or equal to 0.5 μm and less than or equal to 1.4 μm.

It is also preferable that both the lead and terminal portions of the reference electrode have the second thickness which is greater than or equal to 0.5 μm and less than or equal to 1.4 μm.

Preferably, the lead portion of the reference electrode has a circumferential width less than or equal to 9 mm.

Preferably, the entire measurement electrode has a constant thickness which is greater than or equal to 0.7 μm and less than or equal to 1.8 μm.

According to the exemplary embodiments, there is also provided a method of manufacturing the above-described gas sensor element. The method includes a base forming step, a first plating step and a second plating step. In the base forming step, an active base material, which contains an organic platinum complex and a volatile solvent, is applied on a predetermined area of the inner surface of the solid electrolyte body and heat-treated to deposit platinum nuclei on the predetermined area where the reference electrode is to be formed. In the first plating step, a plating solution and a reducing agent are filled into an internal space of the solid electrolyte body so as to immerse only that part of the active base material which is applied on an area of the inner surface of the solid electrolyte body where the large-thickness region is to be formed, thereby depositing platinum only on the area of the inner surface. In the second plating step, a plating solution and a reducing agent are filled into the internal space of the solid electrode body to immerse all the active base material applied on the inner surface of the solid electrolyte body, thereby depositing platinum to form the reference electrode.

With the above method, it is possible to easily and reliably manufacture the above-described gas sensor element.

It is preferable that the plating solution used in the second plating step has a lower concentration than the plating solution used in the first plating step.

In the base forming step, the active base material may be first impregnated into a porous support, which is formed of one of a porous rubber material, a sponge material, a felt material and a fibrous ceramic compact, and then applied on the predetermined area of the inner surface of the solid electrolyte body using the porous support.

It is preferable that the volatile solvent contained in the active base material has a boiling point lower than or equal to 108° C.

According to the exemplary embodiments, there is also provided a gas sensor that includes: the above-described gas sensor element; a heater that is arranged inside the solid electrolyte body of the gas sensor element and generates heat upon being supplied with electric power; a first signal wire for external connection of the gas sensor; a first connector that connects the terminal portion of the reference electrode of the gas sensor element to the first signal wire and holds the heater; a second signal wire for external connection of the gas sensor; a second connector that connects the terminal portion of the measurement electrode of the gas sensor element to the second signal wire; a pair of power supply wires for supplying electric power to the heater; a pair of third connectors that respectively connect the pair of power supply wires to the heater; a tubular housing that receives and holds the solid electrolyte body of the gas sensor element therein; an insulator that insulates and holds the first connector, the second connector and the pair of third connectors; a tubular casing that covers a proximal end portion of the gas sensor element, bundles the first signal wire, the second signal wire and the pair of power supply wires together and hermetically seals those wires; and a cover that covers and thereby protects the detection portion of the gas sensor element which protrudes from a distal end of the housing.

BRIEF DESCRIPTION OF THE DRAWINGS

The present invention will be understood more fully from the detailed description given hereinafter and from the accompanying drawings of exemplary embodiments, which, however, should not be taken to limit the invention to the specific embodiments but are for the purpose of explanation and understanding only.

In the accompanying drawings:

FIG. 4B is a schematic view illustrating problems with a conventional gas sensor element;

FIGS. 5B-5C are tabular representations showing the details of the levels tested in the experimental investigation;

FIG. 6 is a schematic view showing the circumferential width of a lead portion of the reference electrode in each level tested in the experimental investigation;

FIGS. 11A-11C are graphical representations showing the output variations of the levels during the endurance test;

FIG. 13 is a tabular representation showing the condition and results of an experiment conducted by the inventor of the present invention for selecting a preferable solvent for formation of the reference electrode by plating.

DESCRIPTION OF EMBODIMENTS

Figure 1:
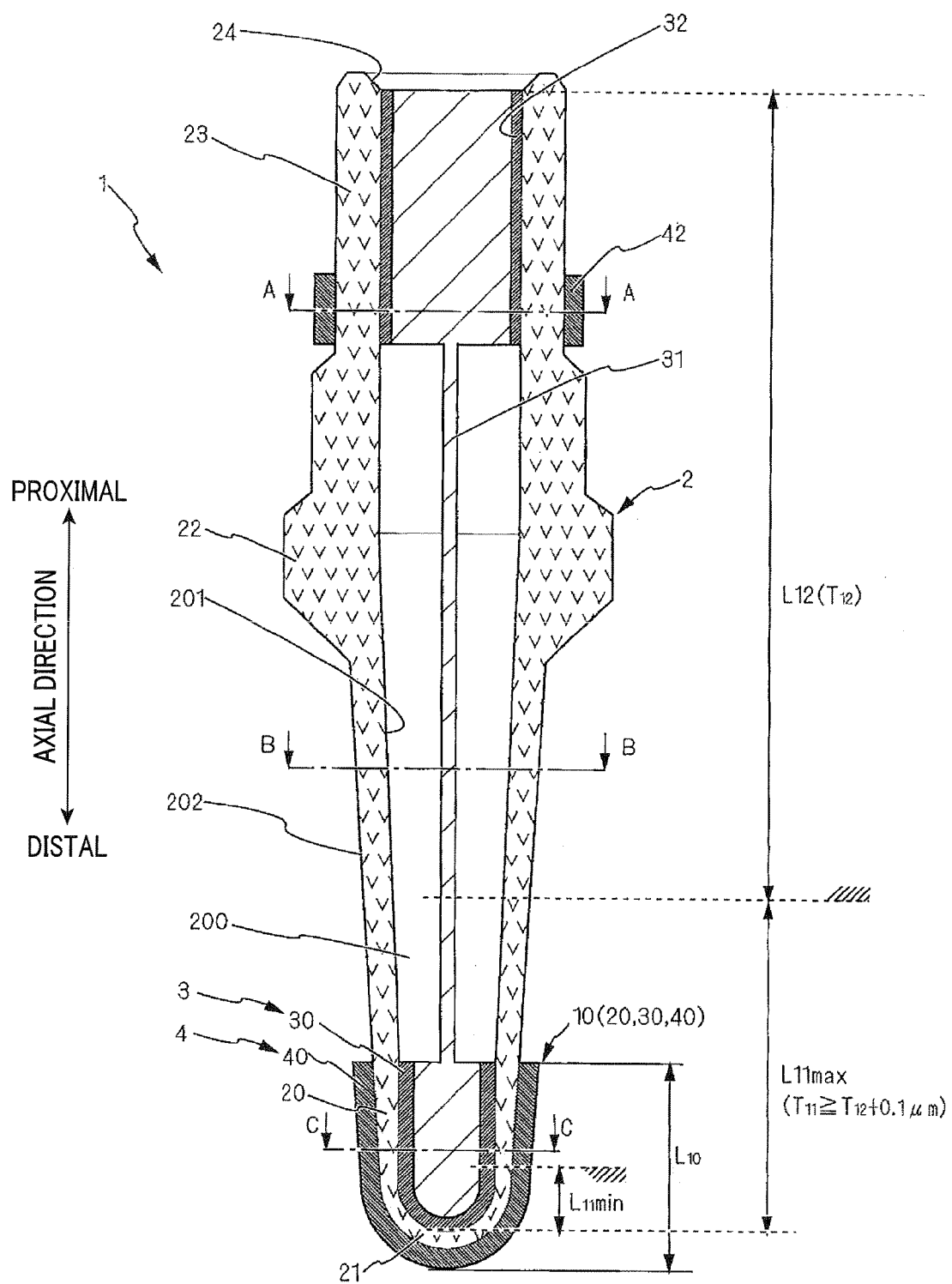
FIG. 1 is a longitudinal cross-sectional view of a gas sensor element according to a first embodiment.
Figure 2A:
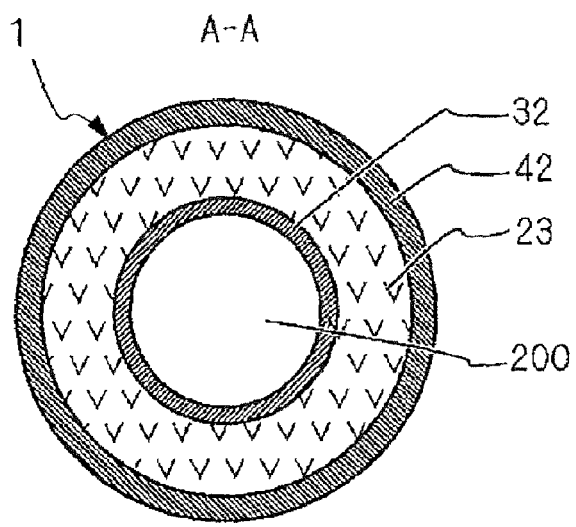
FIG. 2A is a cross-sectional view taken along the line A-A in FIG. 1.
Figure 2B:
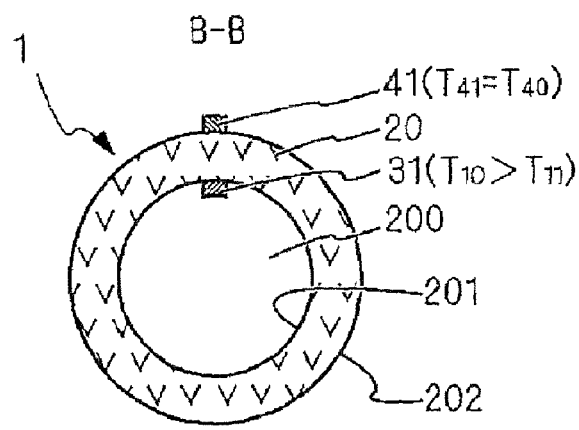
FIG. 2B is a cross-sectional view taken along the line B-B in FIG. 1.
Figure 2C:
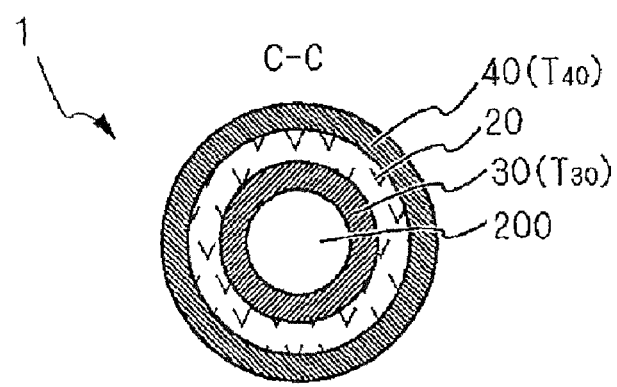
FIG. 2C is a cross-sectional view taken along the line C-C in FIG. 1.
Figure 2D:
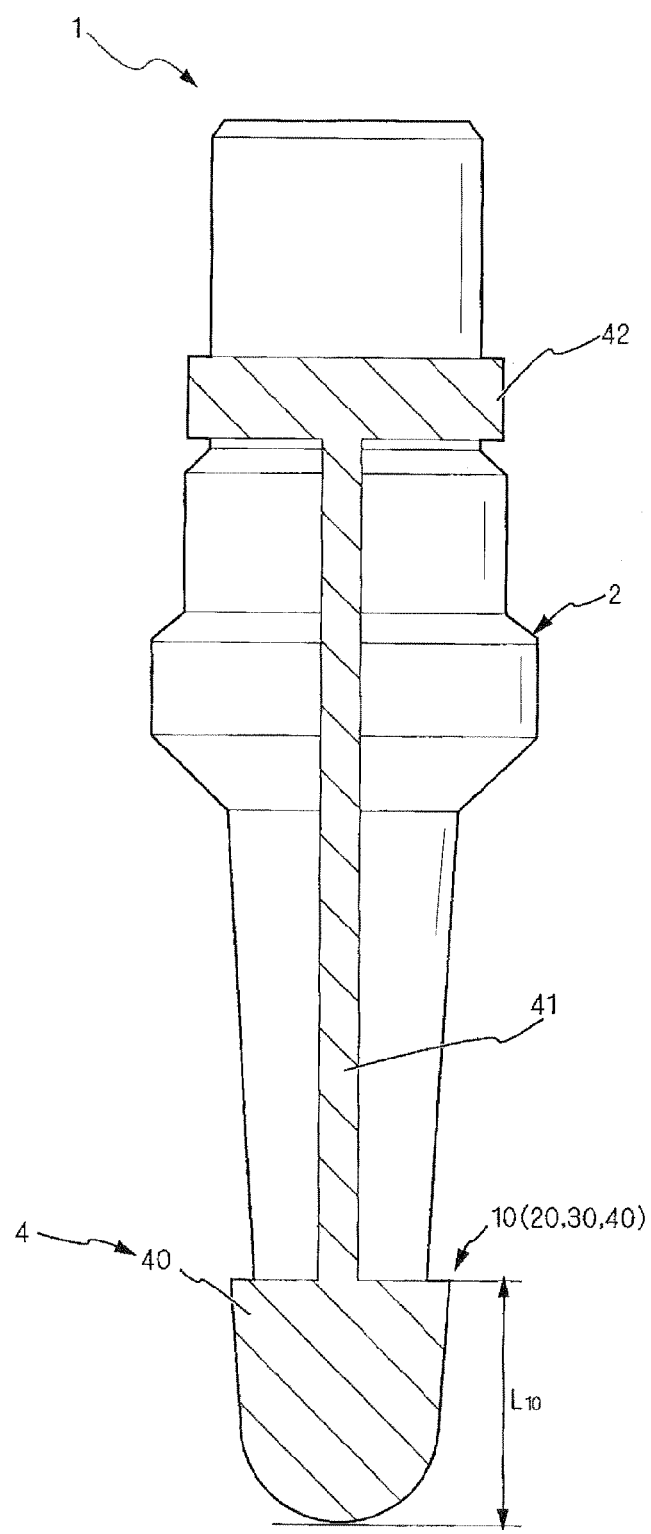
FIG. 2D is a side view of the gas sensor element showing the shape of a measurement electrode of the gas sensor element.

Exemplary embodiments will be described hereinafter with reference to FIGS. 1-14. It should be noted that for the sake of clarity and understanding, identical components having identical functions throughout the whole description have been marked, where possible, with the same reference numerals in each of the figures and that for the sake of avoiding redundancy, descriptions of the identical components will not be repeated.

Referring first to FIGS. 1 and 2A-2D, a gas sensor element 1 according to a first embodiment will be described.

The gas sensor element 1 includes a solid electrolyte body 2 having a cup shape (or bottomed tubular shape), a reference electrode 3 formed on an inner surface 201 of the solid electrolyte body 2, and a measurement electrode 4 formed on an outer surface 202 of the solid electrolyte body 2.

The solid electrolyte body 2 is made, for example, of partially-stabilized zirconia that has oxygen ion conductivity. The solid electrolyte body 2 is formed into the cup shape by a well-known manufacturing method, such as hot pressing.

In addition, it should be appreciated that the solid electrolyte body 2 may also be formed of other solid electrolyte materials, such as a solid electrolyte material having hydrogen ion conductivity.

The solid electrolyte body 2 includes a tubular base portion 20 that opens at a proximal end of the solid electrolyte body 2 and a bottom portion 21 that is closed at a distal end of the solid electrolyte body 2. Moreover, the base portion 20 and the bottom portion 21 together define therein a reference gas chamber 200 into which a reference gas (e.g., air in the present embodiment) is introduced.

On the outer periphery of the solid electrolyte body 2, there is formed an enlarged-diameter portion 22 whose diameter is partially enlarged.

At the proximal end of the solid electrolyte body 2, there is formed a connecting portion 23 for making connection with an external component or device.

On the inner surface 201 of the solid electrolyte body 2, there is formed the reference electrode 3 into a predetermined shape. As will be described in detail later, in the present embodiment, the reference electrode 3 is formed so as to have a larger thickness (or film thickness) at a specific region and a smaller thickness at the remaining region.

On the outer surface 202 of the solid electrolyte body 2, there is formed the measurement electrode 4 at a constant thickness into a predetermined shape.

Each of the reference electrode 3 and the measurement electrode 4 is formed of a porous electrode film whose main component is platinum.

The reference electrode 3 has a detection portion 30, a lead portion 31 and a terminal portion 32.

The detection portion 30 of the reference electrode 3 is formed on the inner surface 201 of the solid electrolyte body 2 over the entire circumference of the inner surface 201.

The lead portion 31 of the reference electrode 3 is formed on the inner surface 201 of the solid electrolyte body 2 into a strip shape. The lead portion 31 extends from the detection portion 30 proximalward in the axial direction of the solid electrolyte body 2 at a constant circumferential width.

In addition, it is preferable that the circumferential width of the lead portion 31 of the reference electrode 3 is greater than or equal to 1 mm, and less than or equal to 84% of the entire circumference of the inner surface 201 of the solid electrolyte body 2 or less than or equal to 9 mm.

The terminal portion 32 of the reference electrode 3 is formed on the inner surface 201 of the solid electrolyte body 2 over the entire circumference of the inner surface 201. The terminal portion 32 extends from the lead portion 31 proximalward in the axial direction of the solid electrolyte body 2.

Moreover, in the reference electrode 3, there are provided both a large-thickness region $L_{11}$ where the reference electrode 3 has a larger thickness (or first thickness) $T_{11}$ and a small-thickness region $L_{12}$ where the reference electrode 3 has a smaller thickness (or second thickness) $T_{12}$.

Specifically, in the present embodiment, the thickness $T_{11}$ in the large-thickness region $L_{11}$ is set to be larger than the thickness $T_{12}$ in the small-thickness region $L_{12}$ by 0.1 μm or more.

Moreover, from an experimental investigation by the inventor of the present invention, it has been made clear that: the thickness $T_{11}$ of the reference electrode 3 in the large-thickness region $L_{11}$ is preferably greater than or equal to 0.6 μm and less than or equal to 1.4 μm; and the thickness $T_{12}$ of the reference electrode 3 in the small-thickness region $L_{12}$ is preferably greater than or equal to 0.5 μm and less than or equal to 1.4 μm.

Furthermore, the large-thickness region $L_{11}$ is preferably set to include at least a region in which when the gas sensor element 1 is heated by a heater 5 to activate the solid electrolyte body 2, the temperature of the reference electrode 3 is within a range of 1.5% from the maximum temperature of the detection portion 30 of the reference electrode 3 (or within a range of 98.5% to 100% of the maximum temperature of the detection portion 30). As will be described in detail later, the heater 5 is arranged inside the solid electrolyte body 2 (see FIG. 3) and generates heat upon being supplied.

Moreover, from the experimental investigation by the inventor of the present invention, it also has been made clear that a proximal end (or an open end-side edge) of the large-thickness region $L_{11}$ is preferably positioned within a range of 5 mm to 20 mm from the distal end of the inner surface 201 of the solid electrolyte body 2. In other words, the distance from the distal end of the inner surface 201 of the solid electrolyte body 2 to the proximal end of the large-thickness region $L_{11}$ is preferably in the range of 5 mm to 20 mm.

On the other hand, the constant thickness of the measurement electrode 4 is preferably set to be in the range of 0.7 μm to 1.8 μm.

Figure 3:
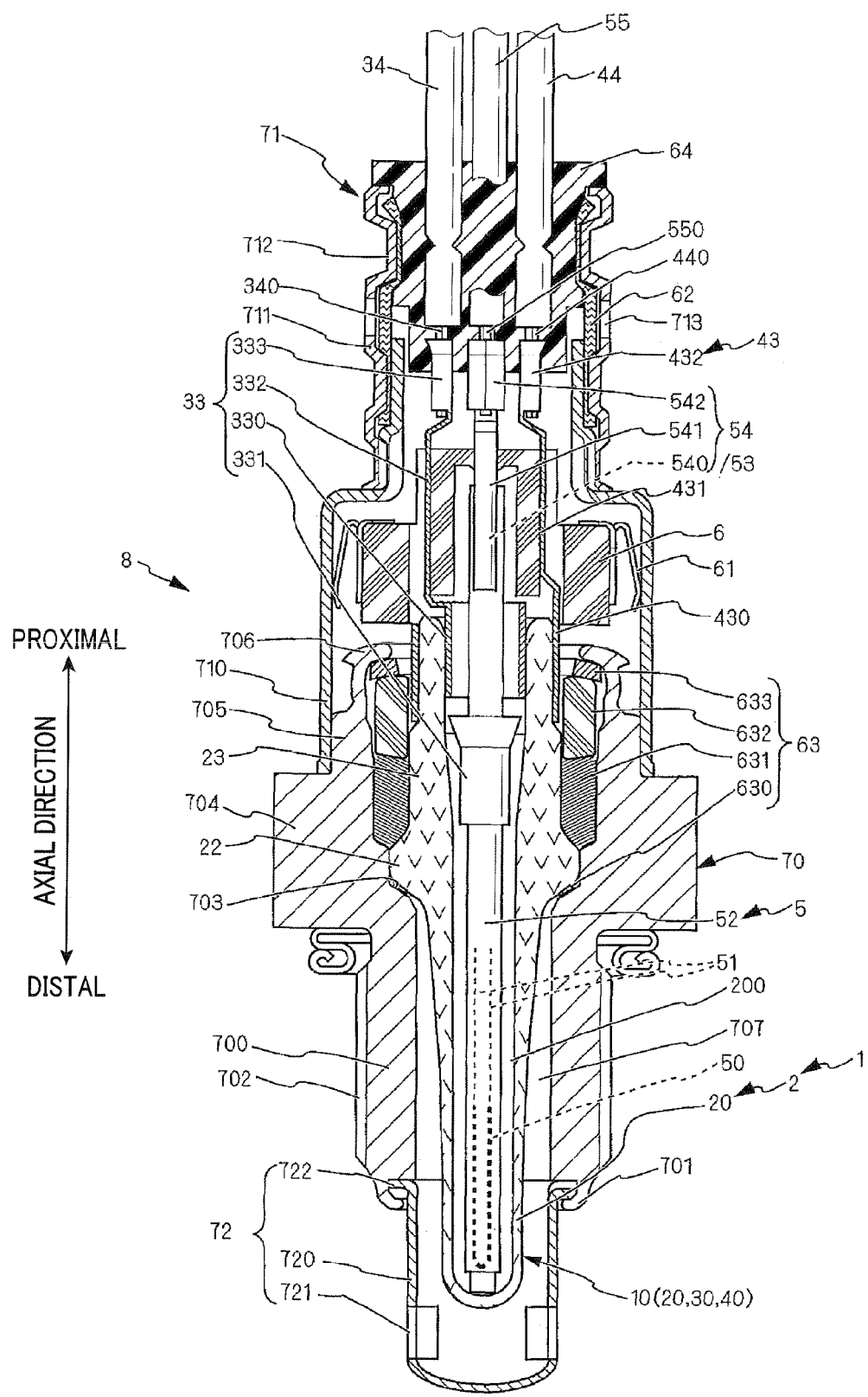
FIG. 3 is a longitudinal cross-sectional view of a gas sensor which includes the gas sensor element according to the first embodiment.

Referring now to FIG. 3, a gas sensor 8 will be described which includes the gas sensor element 1 according to the present embodiment.

The gas sensor 8 is designed to be used in, for example, the exhaust system of an internal combustion engine of a motor vehicle to sense the concentration of a specific component (e.g., oxygen) in the exhaust gas (i.e., the measurement gas) from the engine.

As shown in FIG. 3, the gas sensor 8 includes: the gas sensor element 1; the heater 5 that is arranged inside the solid electrolyte body 2 of the gas sensor element 1 and generates heat upon being supplied with electric power; a first signal wire 34 to be connected to an external device or circuit; a first connector 33 that connects the terminal portion 32 of the reference electrode 3 of the gas sensor element 1 to the first signal wire 34; a second signal wire 44 to be connected to the external device or circuit; a second connector 43 that connects a terminal portion 42 of the measurement electrode 4 of the gas sensor element 1 to the second signal wire 44; a pair of power supply wires 55 for supplying electric power to the heater 5; a pair of third connectors 54 that respectively connect a pair of electrode portions 53 of the heater 5 to the pair of power supply wires 55; a tubular housing 70 that receives and holds the solid electrolyte body 2 of the gas sensor element 1 therein; an insulator 6 that insulates and holds the first connector 33, the second connector 43 and the pair of third connectors 54; a tubular casing 71 that covers a proximal end portion of the gas sensor element 1, bundles the first signal wire 34, the second signal wire 44 and the pair of power supply wires 55 together and hermetically seals those wires 34, 44 and 55; and a cover 72 that covers and thereby protects a detection portion 10 of the gas sensor element 1 which protrudes from a distal end of the housing 70.

Specifically, the housing 70 is made of a well-known refractory metal material which is selected, for example from stainless steel, iron, nickel alloys and carbon steel, according to the environment in which the gas sensor 8 is used. The housing 70 is formed into a tubular shape.

At a distal end of the housing 70, there is formed a crimped portion 701 that is crimped so as to fix the cover 72 to the distal end of the housing 70.

The housing 70 has a tubular base portion 700 which includes the distal end of the housing 70 and receives the gas sensor element 1 therein.

On an outer periphery of the base portion 700, there is formed a threaded portion 702 for fixing the gas sensor 8 to a flow passage of the measurement gas.

The housing 70 further has a hexagonal portion 704 formed on the proximal side of the base portion 700. The hexagonal portion 704 is provided for fastening the threaded portion 702 into a threaded bore (not shown) provided in the flow passage of the measurement gas.

On an inner periphery of the hexagonal portion 704, there is formed a shoulder portion 703 for engaging with and thereby retaining the enlarged-diameter portion 22 of the solid electrolyte body 2 of the gas sensor element 1.

The housing 70 further has a boss portion 705 formed on the proximal side of the hexagonal portion 704. On the boss portion 705, there is fixedly fitted a large-diameter portion 710 of the casing 71.

At a proximal end of the housing 70, there is formed a crimped portion 706 that is crimped so as to elastically press, via a hermetical seal 63, the enlarged-diameter portion 22 of the solid electrolyte body 2 of the gas sensor element 1 against the shoulder portion 703 of the housing 70 and thereby hermetically fix the gas sensor element 1.

The hermetic seal 63 is constituted of metal seal members 630 and 633, a powder seal member (e.g., talc) 631 and an insulative seal member (e.g., alumina) 632.

The casing 71 is made of a well-known refractory metal material such as stainless steel. The casing 71 covers the proximal end portion of the gas sensor element 1, holds the insulator 6 therein, bundles the first signal wire 34, the second signal wire 44 and the pair of power supply wires 55 together via a grommet 64 and thereby hermetically seals the proximal end of the gas sensor 8.

The casing 71 is stepped to have the aforementioned large-diameter portion 710 on the distal side and a small-diameter portion 711 on the proximal side.

As described previously, the large-diameter portion 710 of the casing 71 is fixed on the boss portion 705 of the housing 70.

The small-diameter portion 711 of the casing 71 is fixed, by a crimped portion 712 formed therein, to the grommet 64.

Moreover, a plurality of reference gas holes 713 are formed so as to penetrate the small-diameter portion 711 of the casing 71. In operation, the reference gas is introduced into the reference gas chamber 200 formed in the gas sensor element 1 via the reference gas holes 713.

In addition, a water-repellent filter 62 is provided inside the reference gas introduction holes 713. The water-repellent filter 62 is formed, for example, of a porous body of fluorine fiber which allows gases to pass therethrough while blocking liquids. Consequently, with the water-repellent filter 62, it is possible to prevent water droplets from entering the inside of the gas sensor 8.

The grommet 64 is made of a well-known heat-resistant elastic material, such as fluororubber or silicone rubber. The grommet 64 is formed to have a columnar shape. Further, in the grommet 64, there are formed a plurality of through-holes through which the first signal wire 34, the second signal wire 44 and the pair of power supply wires 55 respectively extend.

The insulator 6 is made of a well-known electrically-insulative material, such as high-purity alumina. The insulator 6 is formed to have a stepped tubular shape. The insulator 6 holds the first connector 33, the second connector 43 and the pair of third connectors 54 so as to electrically insulate them from each other. Moreover, the insulator 6 also electrically insulates the first connector 33, the first signal wire 34, the second connector 43 and the second signal wire 44 from the casing 71.

The first connector 33 is made of a well-known electrically-conductive metal material having superior elasticity, such as stainless steel or an iron-nickel alloy. The first connector 33 includes a contacting portion 330, a heater-holding portion 331, a lead portion 332 and a crimped portion 333.

The contacting portion 330 is arranged so as to be in elastic contact with the terminal portion 32 of the reference electrode 3 provided on the inner surface 201 of the solid electrolyte body 2 of the gas sensor element 1. Consequently, the contacting portion 330 is electrically connected with the terminal portion 32 of the reference electrode 3.

The heater-holding portion 331 elastically grasps the heater 5, thereby holding the heater 5 at a predetermined position inside the solid electrolyte body 2 of the gas sensor element 1.

The lead portion 332 is held in the insulator 6.

The crimped portion 333 is arranged to surround a core conductor 340 of the first signal wire 34 and crimped against the core conductor 340. Consequently, the crimped portion 333 is electrically connected with the first signal wire 34.

The second connector 43 is made of a well-known electrically-conductive metal material having superior elasticity, such as stainless steel or an iron-nickel alloy. The second connector 43 includes a contacting portion 430, a lead portion 431 and a crimped portion 432.

The contacting portion 430 is arranged so as to be in elastic contact with the terminal portion 42 of the measurement electrode 4 provided on the outer surface 202 of the solid electrolyte body 2 of the gas sensor element 1. Consequently, the contacting portion 430 is electrically connected with the terminal portion 42 of the measurement electrode 4.

The lead portion 431 is held in the insulator 6.

The crimped portion 432 is arranged to surround a core conductor 440 of the second signal wire 44 and crimped against the core conductor 440. Consequently, the crimped portion 432 is electrically connected with the second signal wire 44.

The pair of third connectors 54 is made of a well-known electrically-conductive metal material having superior elasticity, such as stainless steel or an iron-nickel alloy. Each of the third connectors 54 includes a contacting portion 540, a lead portion 541 and a crimped portion 542.

The contacting portion 540 is arranged so as to be in elastic contact with a corresponding one of the pair of electrode portions 53 provided on a proximal end portion of the outer surface of the heater 5. Consequently, the contacting portion 540 is electrically connected with the corresponding electrode portion 53 of the heater 5.

The lead portion 541 is held in the insulator 6.

The crimped portion 542 is arranged to surround a core conductor 550 of a corresponding one of the pair of power supply wires 55 and crimped against the core conductor 550. Consequently, the crimped portion 542 is electrically connected with the corresponding power supply wire 55.

The first signal wire 34, the second signal wire 44 and the pair of power supply wires 55 are connected to a not-shown ECU (Electronic Control Unit).

The ECU calculates the concentration of a specific component (e.g., oxygen) in the measurement gas based on the electromotive force or electric current between the reference electrode 3 and the measurement electrode 4. The electromotive force or electric current is caused by the difference between the concentration of oxygen in the reference gas (e.g., air) to which the detection portion 30 of the reference electrode 3 is exposed and the concentration of oxygen in the measurement gas to which a detection portion 40 of the measurement electrode 4 is exposed.

Moreover, the ECU also calculates the temperature of the gas sensor element 1 based on change in the AC impedance between the reference electrode 3 and the measurement electrode 4. Further, the ECU controls electric power supplied to the heater 5 via the pair of power supply wires 55, thereby controlling the temperature of a heating element 50 of the heater 5 to a predetermined temperature.

The heater 5 includes: an insulator 52 which extends in the shape of a shaft; the heating element 50 that is embedded in the insulator 52 and generates heat upon being supplied with electric power; a pair of lead portions 51 for supplying electric power to the heating element 50; and the pair of electrode portions 53 that are formed on the outer surface of the insulator 52 and respectively connected with the pair of lead portions 51.

The heating element 50 is implemented by a well-known electrical resistance heating element, such as tungsten or molybdenum silicide.

The insulator 52 is made of a well-known heat-resistant electrically-insulative material, such as alumina.

The pair of lead portions 51 is made of a well-known electrically-conducive metal material, such as tungsten.

The pair of electrode portions 53 is made of a well-known electrically-conducive metal material, such platinum.

The cover 72 is made of a well-known metal material, such as stainless steel, iron or a nickel alloy. The cover 72 includes a main body 720, a plurality of measurement gas holes 721 and a flange portion 722.

The main body 720 is cup-shaped and arranged to cover the detection portion 10 of the gas sensor element 1 which protrudes from the distal end of the housing 70.

The measurement gas holes 721 are formed through a side wall of the main body 720. In operation, the measurement gas is introduced to the detection portion 10 of the gas sensor element 1 via the measurement gas holes 721.

The flange portion 722 is fixed to the distal end of the housing 70 by the crimped portion 701 of the housing 70.

It should be appreciated that other covers well-known in the art may be employed instead of the above-described cover 72.

For example, in the present embodiment, the single cover 72 is employed to cover the detection portion 10 of the gas sensor element 1. However, a multiple cover may be alternatively employed which consists of two or more coaxially-arranged covers.

Moreover, in the present embodiment, the measurement gas holes 721 are louver-shaped. However, the measurement gas holes 721 may also have other shapes, such as a circular shape.

Furthermore, in the present embodiment, the measurement gas holes 721 are formed through the side wall of the main body 720. However, the measurement gas holes 721 may also be formed through a bottom wall of the main body 720. In addition, the measurement gas holes 721 may also be formed through the side wall of the main body 720 so as to be aligned in two rows that are axially spaced from each other.

Figure 4A:
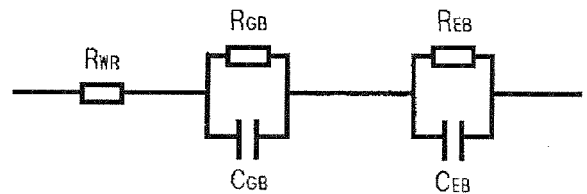
FIG. 4A is a circuit diagram illustrating an equivalent circuit of the complex impedance between reference and measurement electrodes in gas sensor elements.
Figure 4C:
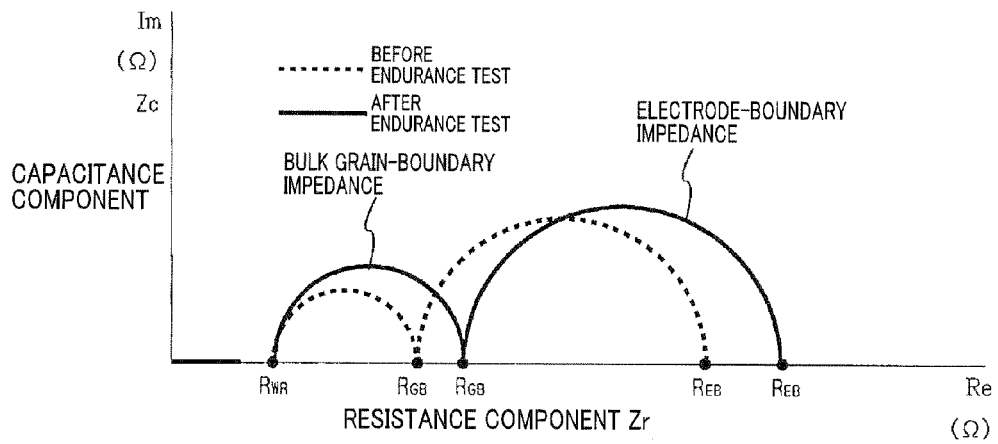
FIG. 4C is a schematic view illustrating advantages of the gas sensor element according to the first embodiment.

Referring now to FIGS. 4A-4C, advantages of the gas sensor element 1 according to the present embodiment over a conventional gas sensor element will be described.

FIG. 4A illustrates an equivalent circuit of the complex impedance Z between the reference electrode 3 and the measurement electrode 4 in gas sensor elements.

As shown in FIG. 4A, the complex impedance Z (i.e., $Zr+j\omega Zc$) between the reference electrode 3 and the measurement electrode 4 is comprised of: a wiring resistance $R_{WR}$ that includes the specific resistances of the reference and measurement electrodes 3 and 4; a bulk grain-boundary impedance that consists of a grain-boundary resistance $R_{GB}$ formed between zirconia particles constituting the solid electrolyte body 2 and a grain-boundary capacitance $C_{GB}$ formed between the zirconia particles in parallel with the grain-boundary resistance $R_{GB}$; and an electrode-boundary impedance that consists of an electrode-boundary resistance $R_{EB}$ formed at boundaries of the reference and measurement electrodes 3 and 4 with the solid electrolyte body 2 and an electrode-boundary capacitance $C_{EB}$ formed at the boundaries in parallel with the electrode-boundary resistance $R_{EB}$.

FIG. 4B shows a complex-impedance plot chart (i.e., so-called Cole-Cole plot) of a conventional gas sensor element in which the reference electrode 3 has a constant thickness. FIG. 4C shows a complex-impedance plot chart of the gas sensor element 1 according to the present embodiment.

Specifically, each of the complex-impedance plot charts shown in FIGS. 4B-4C is obtained by: applying a constant AC voltage between the reference and measurement electrodes 3 and 4; measuring the current when the AC frequency is varied; determining the AC impedance Z between the reference and measurement electrodes 3 and 4; and plotting the AC impedance Z on a complex plane where the axis of abscissa indicates the real component Zr of the impedance Z and the axis of ordinate indicates the imaginary component Zc of the impedance Z.

In addition, in each of the complex-impedance plot charts shown in FIGS. 4B-4C, the initial impedance Z is indicated with dashed lines; the impedance Z after an endurance test is indicated with continuous lines.

As shown in FIG. 4B, with long-term use of the conventional gas sensor element, cohesion of platinum particles constituting the reference electrode 3 occurs, increasing the contact resistance between the platinum particles. At the same time, the capacitance component is also increased with decrease in the surface area of the platinum particles. Consequently, in the conventional gas sensor element, the complex impedance Z between the reference and measurement electrodes 3 and 4 is considerably changed from the initial value thereof. Further, due to the considerable change in the complex impedance Z, when the temperature of the heater 5 is controlled based on the impedance Z, the deviation between a target temperature and the actual temperature of the heater 5 will be increased, thereby causing the sensor output to become unstable.

In comparison, in the gas sensor element 1 according to the present embodiment, the thickness of the reference electrode 3 is set to be large in the large-thickness region $L_{11}$, so as to improve its durability. Consequently, it becomes difficult for atomization to occur in the reference electrode 3. Moreover, the thickness of the reference electrode 3 is set to be small in the lead portion 31 and the terminal portion 32, thereby increasing wiring resistance $R_{WR}$ and thus relatively lowering the influence of change in the electrode-boundary impedance on the entire complex impedance Z.

As a result, as shown in FIG. 4C, the difference between the complex impedance Z between the reference and measurement electrodes 3 and 4 after the endurance test and the initial complex impedance Z is small. Accordingly, with the small change in the complex impedance Z, it is possible to stably control the temperature of the heater 5 based on the impedance Z, thereby improving the reliability of the entire gas sensor 8.

Next, referring to FIGS. 5A-5C, 6 and 7A-7B, the experimental investigation conducted by the inventor of the present invention will be described.

Figure 5A:
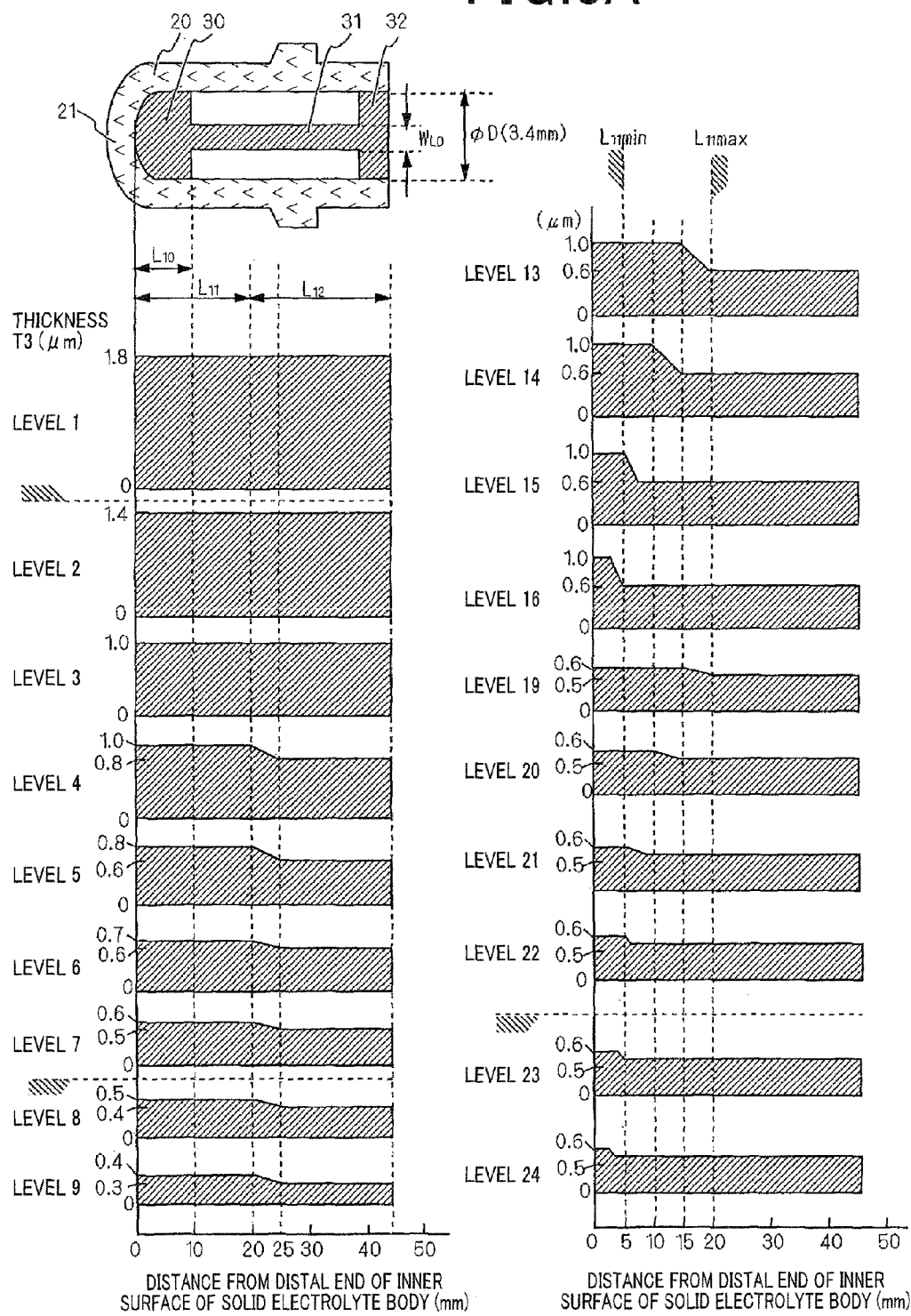
FIG. 5A is a schematic view showing the reference electrode thickness profiles of a plurality of levels (or gas sensor element types) tested in an experimental investigation by the inventor of the present invention.

In the investigation, a total of 33 levels (or gas sensor element types) were tested. FIG. 5A schematically shows the thickness profiles of the reference electrode 3 in the levels tested. FIGS. 5B-5C show in tabular form the details of the levels tested.

Specifically, in each of the levels 1-3, the reference electrode 3 was formed to have a constant thickness over the entire axial length thereof, i.e., from the distal end of the inner surface 201 of the solid electrolyte body 2 to the proximal end of the terminal portion 32 of the reference electrode 3. Moreover, the constant thicknesses of the reference electrode 3 in the levels 1-3 were respectively set to 1.8, 1.4 and 1.0 μm.

In each of the levels 4-9, the large-thickness region $L_{11}$ was set to have an axial length of 20 mm from the distal end of the inner surface 201 of the solid electrolyte body 2. The small-thickness region $L_{12}$ was set to occupy the remaining axial length of the reference electrode 3. Moreover, the thickness $T_{11}$ of the reference electrode 3 in the large-thickness region $L_{11}$ was set to 1.0, 0.8, 0.7, 0.6, 0.5 and 0.4 μm respectively for the levels 4-9. The thickness $T_{12}$ of the reference electrode 3 in the small-thickness region $L_{12}$ was set to 0.8, 0.6, 0.6, 0.5, 0.4 and 0.3 μm respectively for the levels 4-9.

For the levels 10-12, the constant thickness of the measurement electrode 4 provided on the outer surface 202 of the solid electrolyte body 2 was varied as shown in FIGS. 5B-5C.

For the levels 13-24, the axial length of the large-thickness region $L_{11}$ and the thickness $T_{11}$ of the reference electrode 3 in the large-thickness region $L_{11}$ were varied as shown in FIGS. 5A-5C, so as to find the critical significance.

FIG. 6 shows the circumferential width W of the lead portion 31 of the reference electrode 3 in the levels 1-33 tested in the experimental investigation.

In addition, in the experimental investigation, the inner diameter D of the solid electrolyte body 2 was equal to 3.4 mm. However, the present invention is not limited to this experimental condition.

As shown in FIG. 6, in each of the levels 1-26 and 32-33, the circumferential width W of the lead portion 31 of the reference electrode 3 was set to 1 mm.

In the levels 27-29, the circumferential width W of the lead portion 31 of the reference electrode 3 was set to 3, 6 and 9 mm, respectively.

In each of the levels 30 and 31, the lead portion 31 of the reference electrode 3 was formed over the entire circumference of the inner surface 201 of the solid electrolyte body 2.

Moreover, in the levels 10, 11, 12, 32 and 33, the constant thickness of the measurement electrode 4 provided on the outer surface 202 of the solid electrolyte body 2 was set to 1.4, 1.8, 2.2, 0.7 and 0.6 μm, respectively.

In all the other levels than the above-described levels 10-12 and 32-33, the constant thickness of the measurement electrode 4 was set to 0.8 μm.

In the experimental investigation, for each of the levels 1-33, the initial impedance Z between the reference and measurement electrodes 3 and 4 was measured at 500, 600 and 700° C. Then, each of the levels 1-33 was subjected to an endurance test of 1600 hours. Thereafter, for each of the levels 1-33, the impedance Z between the reference and measurement electrodes 3 and 4 was measured again at 600° C. In addition, the output variation during the endurance test was also measured for each of the levels 1-33.

Figure 7A:
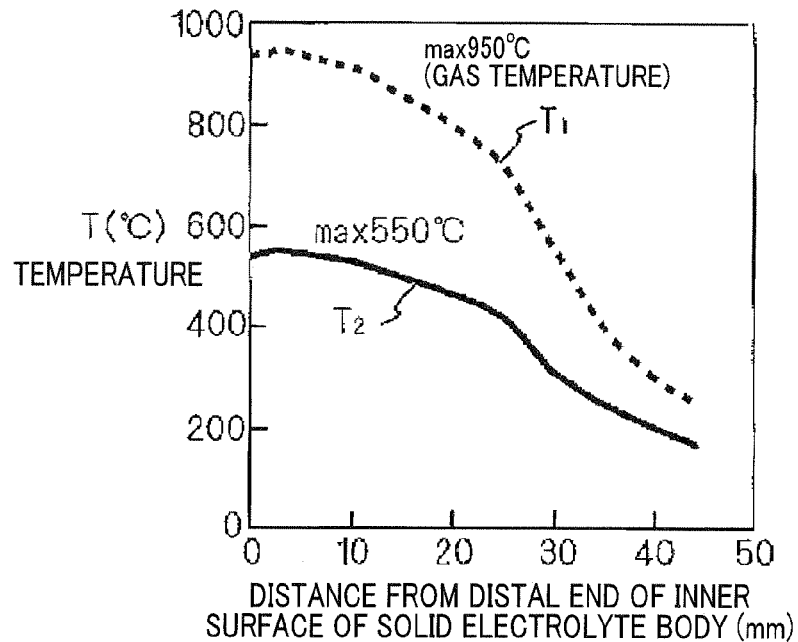
FIG. 7A is a graphical representation illustrating the relationship between the temperature of the gas sensor element according to the first embodiment and the temperature of a measurement gas measured by the gas sensor element.

FIG. 7A shows the relationship between the temperature $T_1$ of the measurement gas and the temperature $T_2$ of the gas sensor element 1 when a propane gas heated to 950° C. is used to simulate the measurement gas. More specifically, when the temperature $T_1$ of the measurement gas changes with change in axial distance from the distal end of the gas sensor element 1 as indicated with the broken line in FIG. 7A, the temperature $T_2$ of the gas sensor element 1 changes with change in axial distance from the distal end of the gas sensor element 1 as indicated with the continuous line in FIG. 7A. In addition, the maximum value of the temperature $T_2$ of the gas sensor element 1 is equal to 550° C. when the maximum value of the temperature $T_1$ of the measurement gas is equal to 950° C.

Figure 7B:
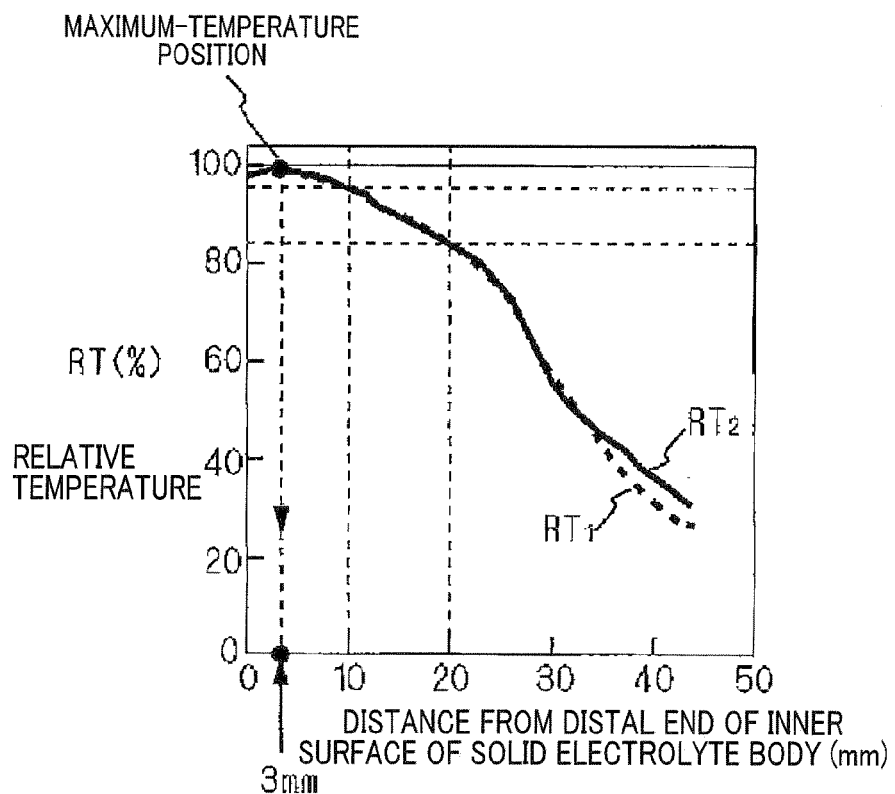
FIG. 7B is a graphical representation illustrating the relationship upon converting both the temperature of the gas sensor element and the temperature of the measurement gas into relative temperatures to their respective maximum values.
Figure 8A:
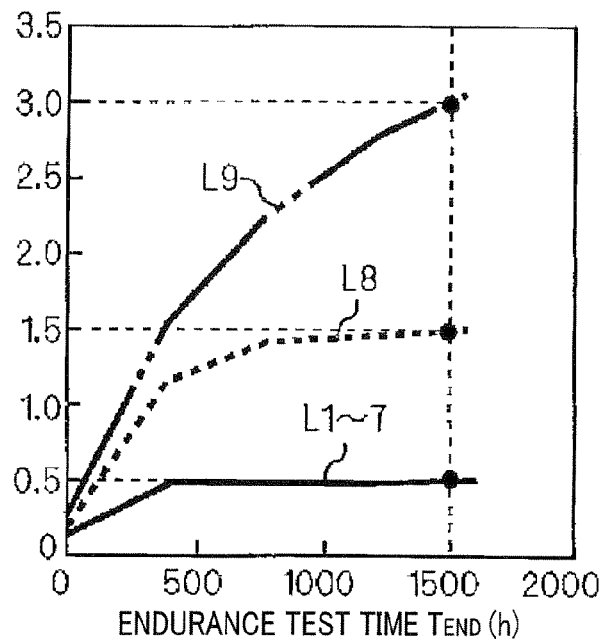
FIG. 8A is a graphical representation showing the effect of the thickness of the reference electrode in a large-thickness region on change in the impedance between the reference and measurement electrodes due to an endurance test.
Figure 8B:
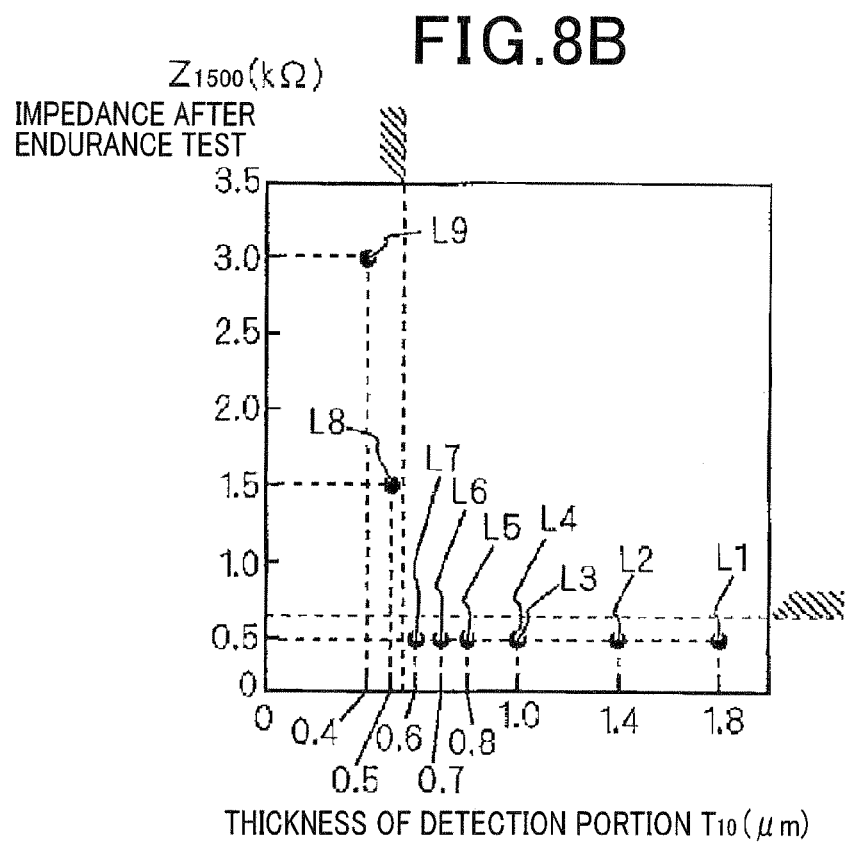
FIG. 8B is a graphical representation showing a criticality in the thickness of a detection portion of the reference electrode.
Figure 9A:
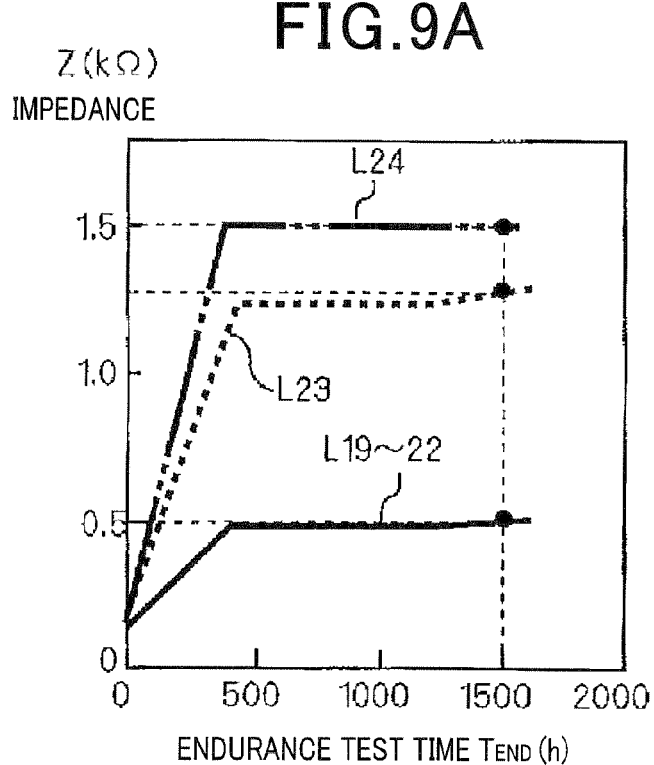
FIG. 9A is a graphical representation showing the effect of the position of a proximal end of the large-thickness region on change in the impedance between the reference and measurement electrodes due to the endurance test.
Figure 9B:
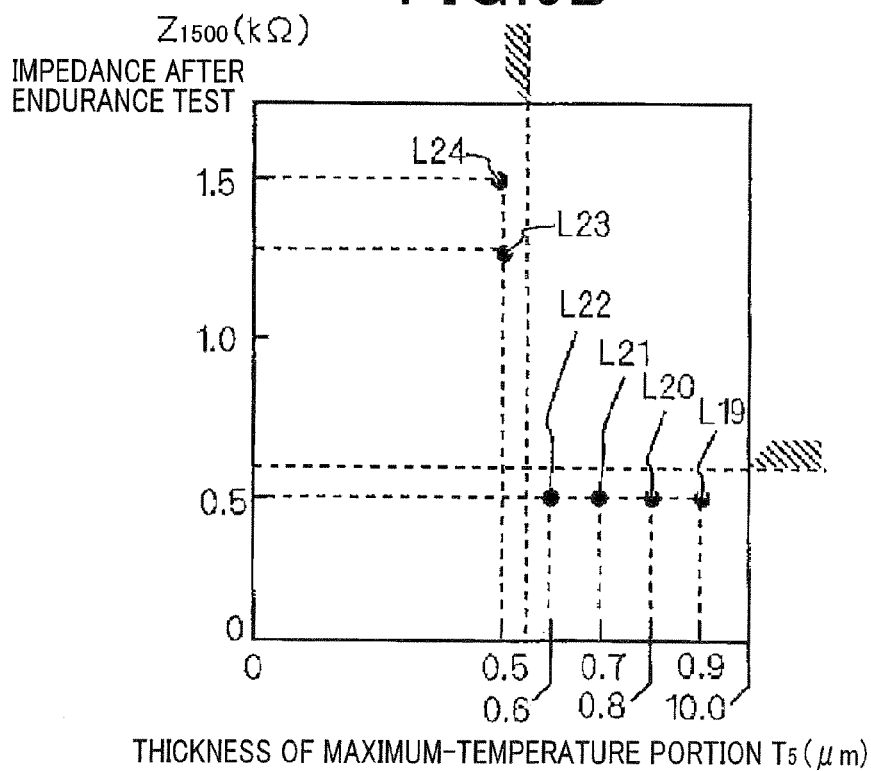
FIG. 9B is a graphical representation showing a criticality in the thickness of a maximum-temperature portion of the reference electrode.

FIG. 7B is obtained by converting the temperature $T_1$ of the measurement gas and the temperature $T_2$ of the gas sensor element 1 into the relative temperature $RT_1$ of the measurement gas and the relative temperature $RT_2$ of the gas sensor element 1 to their respective maximum values.

As seen from FIG. 7B, the change in the relative temperature $RT_1$ of the measurement gas and the change in the relative temperature $RT_2$ of the gas sensor element 1 almost coincide with each other.

Moreover, it has been made clear that: the temperature $T_2$ of the gas sensor element 1 is highest at an axial position away from the distal end of the inner surface 201 of the solid electrolyte body 2 by 3 mm. It also has been made clear that the temperature $T_2$ of the gas sensor element 1 in the detection portion 10 is higher than or equal to 96% of the maximum value of the temperature $T_2$.

In addition, the detection portion 10 of the gas sensor element 1 is comprised of the detection portion 30 of the reference electrode 3, the detection portion 40 of the measurement electrode 4, and that portion of the solid electrolyte body 2 which is interposed between the detection portions 30 and 40 of the reference and measurement electrodes 3 and 4 (see FIG. 1).

The results of the experimental investigation conducted by the inventor of the present invention are shown in FIGS. 5B-5C, 8A-8B, 9A-9B, 10, 11A-11C and 12.

From the experimental results of the levels 1-9 shown in FIGS. 5B-5C and 8A-8B, it has been made clear that the thickness $T_{11}$ of the reference electrode 3 in the large-thickness region $L_{11}$ has a criticality between 0.5 and 0.6 μm.

More specifically, in FIGS. 5B-5C, the levels 8-9, whose impedances were considerably changed and durability was lowered, are evaluated as "x" (i.e., very poor). In contrast, the levels 1-7, whose impedance changes were small, are evaluated as "○" (i.e., good).

That is, when the thickness $T_{11}$ of the reference electrode 3 in the large-thickness region $L_{11}$ was less than or equal to 0.5 μm, the impedance between the reference and measurement electrodes 3 and 4 was considerably changed by the endurance test. In contrast, when the thickness $T_{11}$ of the reference electrode 3 in the large-thickness region $L_{11}$ was greater than or equal to 0.6 μm, it was possible to suppress change in the impedance between the reference and measurement electrodes 3 and 4 due to the endurance test and thus possible to suppress the atomization of the reference electrode 3 due to the endurance test.

Moreover, as can be seen from FIGS. 5B-5C and 9A-9B, it is preferable that the proximal end of the large-thickness region $L_{11}$ be positioned away from the distal end of the inner surface 201 of the solid electrolyte body 2 by 5 mm or more.

More specifically, when the proximal end of the large-thickness region $L_{11}$ was positioned away from the distal end of the inner surface 201 of the solid electrolyte body 2 by 3 mm or less as in the levels 17-18, the impedance between the reference and measurement electrodes 3 and 4 was considerably changed by the endurance test. Consequently, even with the thickness $T_{11}$ of the reference electrode 3 in the large-thickness region $L_{11}$ set to 1 μm, it was still impossible to secure the durability of the reference electrode 3.

Moreover, the durability of the level 23 was lowered by the endurance test; in the level 23, the thickness $T_{11}$ of the reference electrode 3 in the large-thickness region $L_{11}$ was 0.6 µm and the proximal end of the large-thickness region $L_{11}$ was positioned away from the distal end of the inner surface 201 of the solid electrolyte body 2 by 3 mm (i.e., by less than 5 mm). In contrast, the durability of the level 22 could be secured; in the level 22, the thickness $T_{11}$ of the reference electrode 3 in the large-thickness region $L_{11}$ was also 0.6 µm but the proximal end of the large-thickness region $L_{11}$ was positioned away from the distal end of the inner surface 201 of the solid electrolyte body 2 by 5 mm.

In FIGS. 5B-5C, the levels 19-22 are evaluated as "○", and the levels 17-18 and 23-24 are evaluated as "x".

On the other hand, when the proximal end of the large-thickness region $L_{11}$ was positioned away from the distal end of the inner surface 201 of the solid electrolyte body 2 by more than 20 mm, no further improvement of the durability of the reference electrode 3 was observed. Accordingly, it has been made clear that to reduce the amount of platinum used for formation of the reference electrode 3, the proximal end of the large-thickness region $L_{11}$ is preferably positioned away from the distal end of the inner surface 201 of the solid electrolyte body 2 by 20 mm or less.

Figure 10:
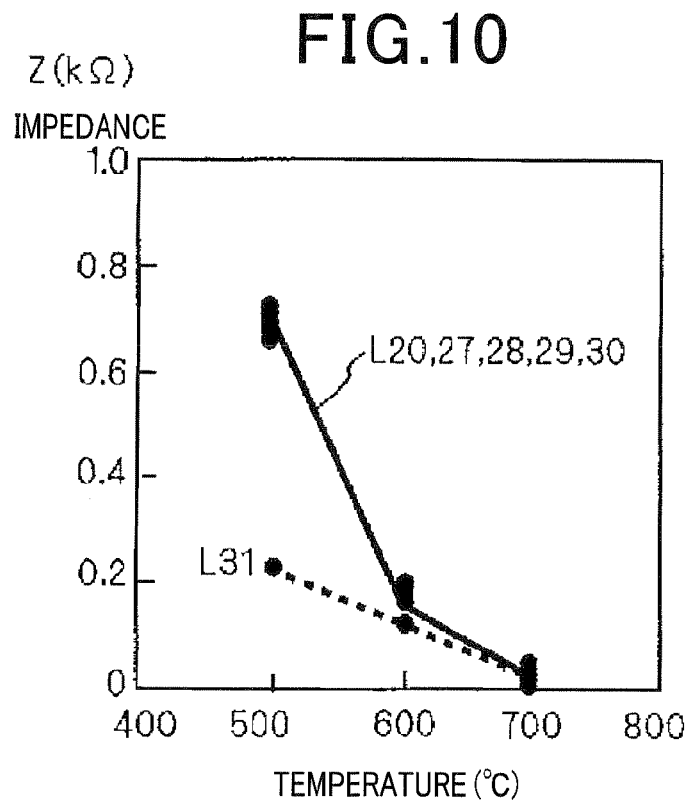
FIG. 10 is a graphical representation showing the effect of the circumferential width of the lead portion of the reference electrode on change in the impedance between the reference and measurement electrodes due to the endurance test.

FIG. 10 illustrates the effect of the circumferential width W of the lead portion 31 of the reference electrode 3 on change in the impedance Z between the reference and measurement electrodes 3 and 4.

As seen from FIG. 10, when the lead portion 31 of the reference electrode 3 was formed over the entire circumference of the inner surface 201 of the solid electrolyte body 2 as in the level 31, the temperature gradient of the resistance component of the impedance Z was small. In contrast, when the lead portion 31 of the reference electrode 3 was formed to have a circumferential width W less than or equal to 9 mm as in the levels 20 and 27-30, the temperature gradient of the resistance component of the impedance Z was large.

That is, in the levels 20 and 27-30, a small temperature change could cause the impedance Z to considerably change. Therefore, in terms of accuracy in controlling the temperature of the heater 5 (or the temperature of the gas sensor element 1) based on the impedance Z, it is preferable for the circumferential width W of the lead portion 31 of the reference electrode 3 to be less than or equal to 9 mm.

Figure 11A:
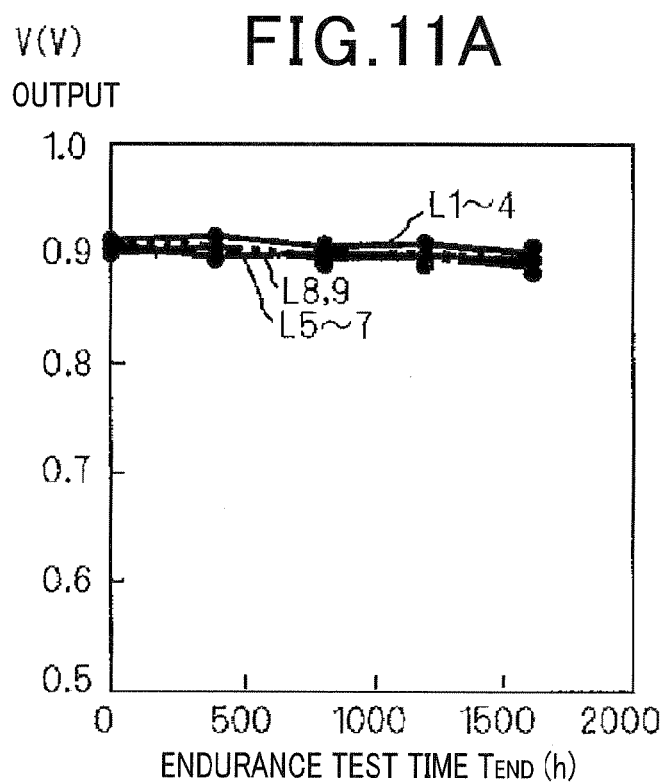

FIG. 11A illustrates the output variations of the levels 1-9 during the endurance test.

As seen from FIG. 11A, the outputs of the levels 1-9 were almost unchanged with time during the endurance test. That is, all the levels 1-9 had high durability.

However, in the levels 1-3, the amount of platinum used for formation of the reference electrode 3 was large. Therefore, in terms of manufacturing cost, the levels 1-3 are evaluated as "x" (i.e., very poor) or "Δ" (i.e., poor) in FIGS. 5B-5C.

Accordingly, it has been made clear that the levels 5-7 are preferable in terms of both durability and manufacturing cost.

FIG. 11B illustrates the output variations of the levels 3 and 13-18 during the endurance test.

As seen from FIG. 11B, the outputs of the levels 17-18 were considerably changed with time during the endurance test. Moreover, as described previously, in the levels 17-18, the impedance between the reference and measurement electrodes 3 and 4 was also considerably changed by the endurance test. Therefore, in FIGS. 5B-5C, the levels 17-18 are evaluated as "x".

In addition, in the levels 17-18, the large-thickness region $L_{11}$ was formed within 5 mm from the distal end of the inner surface 201 of the solid electrolyte body 2. Therefore, it is inferred that in the levels 17-18, atomization of the detection portion 30 of the reference electrode 3 was progressed with the endurance test, causing the outputs of the levels 17-18 to change.

In contrast, the outputs of the levels 3, 13-16 and 19-22 were almost unchanged with time during the endurance test. Moreover, in levels 3, 13-16 and 19-22, change in the impedance between the reference and measurement electrodes 3 and 4 due to the endurance test was small.

FIG. 11C illustrates the output variations of the levels 7 and 32-33 during the endurance test.

In the levels 7 and 32-33, the constant thickness of the measurement electrode 4 was set to 0.8, 0.7 and 0.6, respectively.

From FIG. 11C, it has been made clear that durability can be improved by setting the constant thickness of the measurement electrode 4 to be 0.7 µm or more.

Figure 12:
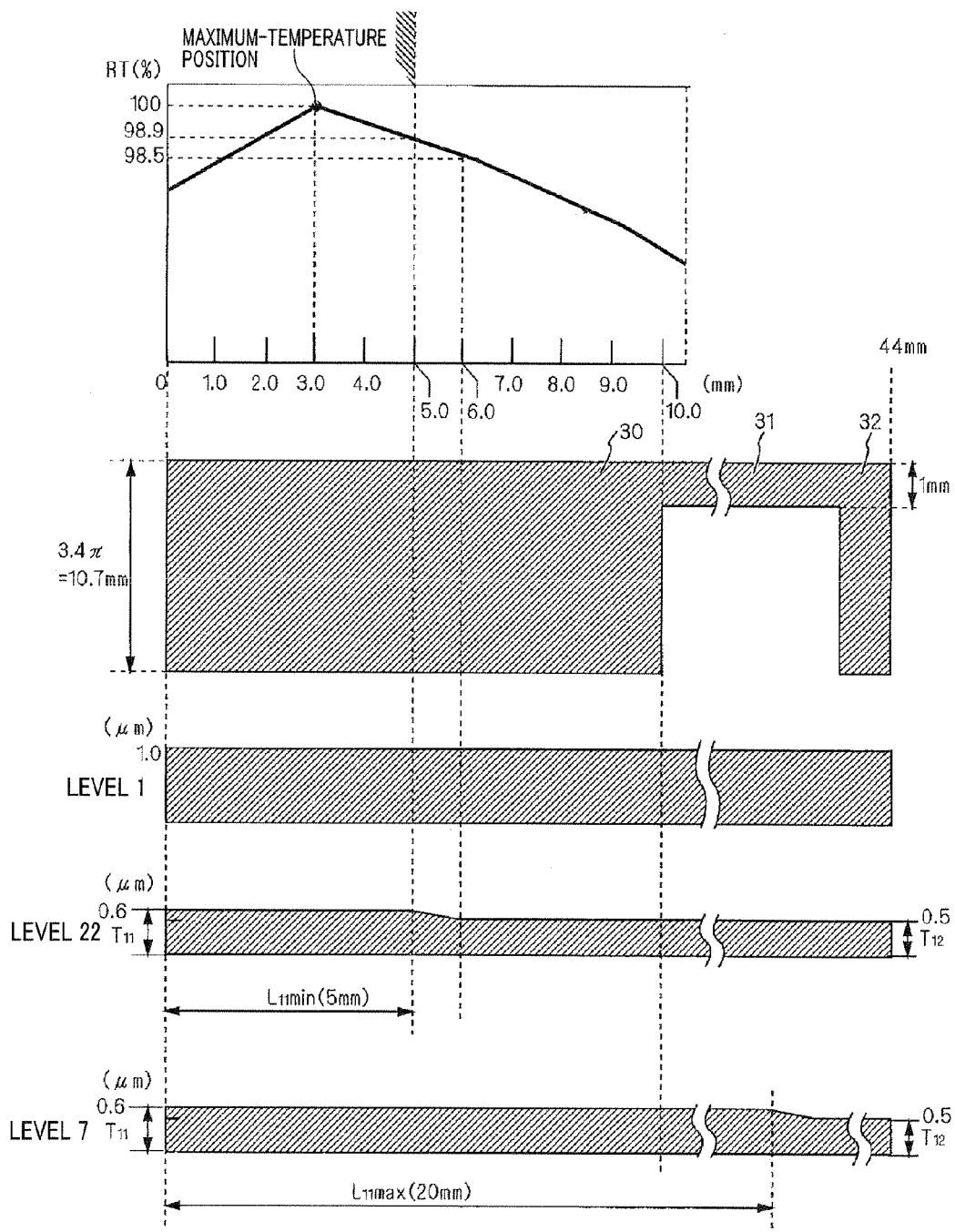
FIG. 12 is a schematic view summarizing the findings of the experimental investigation about the preferable shape and thickness of the reference electrode.

FIG. 12 summarizes the findings of the experimental investigation about the preferable shape and thickness of the reference electrode 3.

As shown in FIG. 12, the temperature of the gas sensor element 1 is highest around the axial position away from the distal end of the inner surface 201 of the solid electrolyte body 2 by 3 mm.

The axial position away from the distal end of the inner surface 201 of the solid electrolyte body 2 by 5 mm is a critical position of the proximal end of the large-thickness region $L_{11}$ for improving the durability of the reference electrode 3. Therefore, it is possible to improve the durability of the reference electrode 3 by setting the large-thickness region $L_{11}$ to include at least a region in which the temperature of the reference electrode 3 is within a range of 1.5% from the maximum temperature of the gas sensor element 1.

Moreover, it is preferable that $L_{11}\mathrm{min} \geq 5$ mm, where $L_{11}\mathrm{min}$ is a minimum axial length of the large-thickness region $L_{11}$ from the distal end of the inner surface 201 of the solid electrolyte body 2.

It is also preferable that $L_{11}\mathrm{max} \leq 20$ mm, where $L_{11}\mathrm{max}$ is a maximum axial length of the large-thickness region $L_{11}$ from the distal end of the inner surface 201 of the solid electrolyte body 2.

It is also preferable that $0.6\ \mu\mathrm{m} \leq T_{11} \leq 1.4\ \mu\mathrm{m}$ and $0.5\ \mu\mathrm{m} \leq T_{12} \leq 1.4\ \mu\mathrm{m}$, where $T_{11}$ is the thickness of the reference electrode 3 in the large-thickness region $L_{11}$ and $T_{12}$ is the thickness of the reference electrode 3 in the small-thickness region $L_{12}$.

Next, a method of manufacturing the gas sensor element 1 according to the present embodiment will be described.

It should be noted that the components of the gas sensor element 1 other than the reference electrode 3 may be manufactured using methods well-known in the art. For example, the solid electrolyte body 2 may be formed into the cup shape by hot pressing partially-stabilized zirconia.

Accordingly, for the sake of avoiding redundancy, only steps for manufacturing the reference electrode 3 will be described hereinafter.

In the present embodiment, the method of manufacturing the gas sensor element 1 includes a base forming step P0, a first plating step P1 and a second plating step P2.

In the base forming step P0, an active base material, which contains an organic platinum complex and a volatile solvent, is applied on a predetermined area of the inner surface 201 of the solid electrolyte body 2. Then, the base material is subjected to a heat treatment, depositing platinum nuclei in a desired shape on that predetermined area of the inner surface 201 of the solid electrolyte body 2 where the reference electrode 3 is to be formed.

Specifically, in this step, the active base material is first impregnated into a porous support that is formed, for example of a porous rubber material, a sponge material, a felt material or a fibrous ceramic compact, into a predetermined shaped. Then, the porous support is used like a pen nib to apply the active base material on the predetermined area of the inner surface 201 of the solid electrolyte body 2.

More specifically, referring again to FIG. 1, for an area of the inner surface 201 of the solid electrolyte body 2 where the detection portion 30 of the reference electrode 3 is to be formed, the porous support is rotated along the circumferential direction of the solid electrolyte body 2 with a tip of the support pressed on the area of the inner surface 201, thereby applying the active base material over the entire circumference of the inner surface 201.

Moreover, for an area of the inner surface 201 of the solid electrolyte body 2 where the lead portion 31 of the reference electrode 3 is to be formed, the porous support is linearly moved in the axial direction of the solid electrolyte body 2 with the tip of the support pressed on the area of the inner surface 201, thereby applying the active base material at a constant circumferential width.

Furthermore, for an area of the inner surface 201 of the solid electrolyte body 2 where the terminal portion 32 of the reference electrode 3 is to be formed, the porous support is rotated along the circumferential direction of the solid electrolyte body 2 with the tip of the support pressed on the area of the inner surface 201, thereby applying the active base material over the entire circumference of the inner surface 201.

The inventor of the present invention have found, through an experiment, that the boiling point of the volatile solvent contained in the active base material is preferably lower than or equal to 108° C. The results of the experiment will be described later with reference to FIG. 13.

In the first plating step P1, a plating solution and a reducing agent are filled into the internal space of the solid electrolyte body 2 so as to immerse only that part of the active base material which is applied on an area of the inner surface 201 of the solid electrolyte body 2 where the large-thickness region $L_{11}$ is to be formed, thereby depositing platinum only on the area of the inner surface 201.

More specifically, in this step, the solid electrolyte body 2 is placed with its open end facing upward. Then, the plating solution and the reducing agent are filled into the internal space of the solid electrode body 2 from the open end thereof to such a height as to immerse only that part of the active base material which is applied on the area of the inner surface 201 of the solid electrolyte body 2 where the large-thickness region $L_{11}$ is to be formed. Consequently, platinum is deposited at a constant thickness only on the area of the inner surface 201 of the solid electrolyte body 2 where the large-thickness region $L_{11}$ is to be formed.

In the second plating step P2, a plating solution and a reducing agent are filled into the internal space of the solid electrode body 2 to immerse all the active base material applied on the inner surface 201 of the solid electrolyte body 2, thereby depositing platinum to form the reference electrode 3.

Consequently, in the finally-obtained reference electrode 3, the thickness $T_{11}$ of the reference electrode 3 in the large-thickness region $L_{11}$ where platinum has been deposited twice in the first and second plating steps P1 and P2 is larger than the thickness $T_{12}$ of the reference electrode 3 in the remaining region (i.e., the small-thickness region $L_{12}$) where platinum has been deposited only once in the second plating step P2.

In addition, plating is not performed on any area of the inner surface 201 of the solid electrolyte body 2 where no active base material is applied. Accordingly, the reference electrode 3 is formed only in the predetermined area of the inner surface 201 of the solid electrolyte body 2 where the active base material is applied.

Moreover, by setting the concentration of the plating solution used in the second plating step P2 to be lower than that of the plating solution used in the first plating step P1, it is possible to increase the difference between the thickness $T_{11}$ of the reference electrode 3 in the large-thickness region $L_{11}$ and the thickness $T_{12}$ of the reference electrode 3 in the small-thickness region $L_{12}$, thereby reducing the amount of platinum used for the entire reference electrode 3.

Furthermore, in the second plating step P2, the amount of the plating solution filled into the internal space of the solid electrolyte body 2 may be increased in stages to the axial location of the terminal portion 32 of the reference electrode 3. In this case, it is possible to decrease in stages the thicknesses of the lead portion 31 and the terminal portion 32 of the reference electrode 3 which are subjected to relatively low ambient temperature, thereby further reducing the amount of platinum used for formation of the reference electrode 3. Moreover, it is also possible to further increase the resistance of the reference electrode 3, thereby lowering the influence of the impedance increase when atomization of the detection portion 30 of the reference electrode 3 is caused by long-term use of the gas sensor element 1.

Referring back to FIG. 2D, in the present embodiment, the measurement gas 4 is formed on the outer surface 202 of the solid electrolyte body 2 at a constant thickness. The constant thickness of the measurement electrode 4 is in the range of, for example, 0.7 μm to 1.4 μm. The measurement gas 4 has the detection portion 40, a lead portion 41 and the terminal portion 42.

The detection portion 40 of the measurement electrode 4 is formed on the outer surface 202 of the solid electrolyte body 2 over the entire circumference of the outer surface 202.

The lead portion 41 of the measurement electrode 4 is formed on the outer surface 202 of the solid electrolyte body 2 into a strip shape. The lead portion 41 extends from the detection portion 40 proximalward in the axial direction of the solid electrolyte body 2 at a constant circumferential width. The constant circumferential width of the lead portion 41 is in the range of, for example, 0.5 to 4 mm.

In addition, the measurement electrode 4 may also have two lead portions 42 that are circumferentially spaced from each other by 180°.

The terminal portion 42 of the measurement electrode 4 is formed on the outer surface 202 of the solid electrolyte body 2 over the entire circumference of the outer surface 202. The terminal portion 42 extends from the lead portion 41 proximalward in the axial direction of the solid electrolyte body 2.

In the present embodiment, the measurement electrode 4 is formed by: applying an active base material on a predetermined area of the outer surface 202 of the solid electrolyte body 2 where the measurement electrode 4 is to be formed; performing a heat treatment on the applied active base material; and immersing the outer surface 202 of the solid electrolyte body 2 in the mixture of a plating solution and a reducing agent to deposit platinum on the predetermined area of the outer surface 202. In addition, the active base material is applied on the predetermined area of the outer surface 202 of the solid electrolyte body 2 using a porous support impregnated with the active base material as in the above-described base forming step P0.

With the above method, it is possible to more easily form the measurement electrode 4 in comparison with conventional methods. In addition, since the location of the measurement electrode 4 is on the outer surface 202 of the solid electrolyte body 2, the measurement electrode 4 may also be formed with a conventional method.

Next, explanation will be made of the experiment conducted by the inventor of the present invention for selecting a preferable solvent for the active base material used for formation of the reference electrode 3.

In the experiment, each of eight organic solvents as shown in FIG. 13 was tested in the following way.

First, platinum complex was dissolved in the organic solvent to form the active base material. Then, the active base material was impregnated into the porous support that was formed of a felt material to have a width of 1.5 mm. Thereafter, using the porous support, the active base material was applied on the inner surface 201 of the solid electrolyte body 2, which was placed sideways, into a predetermined shape. Then, the solid electrolyte body 2 was placed to stand vertically, and the applied active base material was dried.

Further, the applied active base material was heat-treated at a temperature in the range of 400 to 500° C., depositing platinum nuclei on the inner surface 201 of the solid electrolyte body 2. Then, plating was performed by immersing the solid electrolyte body 2 in the mixture of a plating solution and a reducing agent. Thereafter, the organic solvent was evaluated in terms of plating line width, plating bleed, dripping of the active base material.

The results of the experiment are shown in FIG. 13.

As can been seen from FIG. 13, in terms of dispersion of the active base material, it is preferable to use a volatile solvent whose boiling point is lower than or equal to 108° C. for the active base material. In this case, it is possible to quickly dry the active base material, keep the active base material in a desired shape and form a plating layer without causing occurrence of plating bleed.

In contrast, in the case of terpineol, it took a long time to dry the active base material. Thus, during the drying, the active base material spread on the inner surface 201 of the solid electrolyte body 2, making it difficult to keep the active base material in a desired shape.

Figure 14:
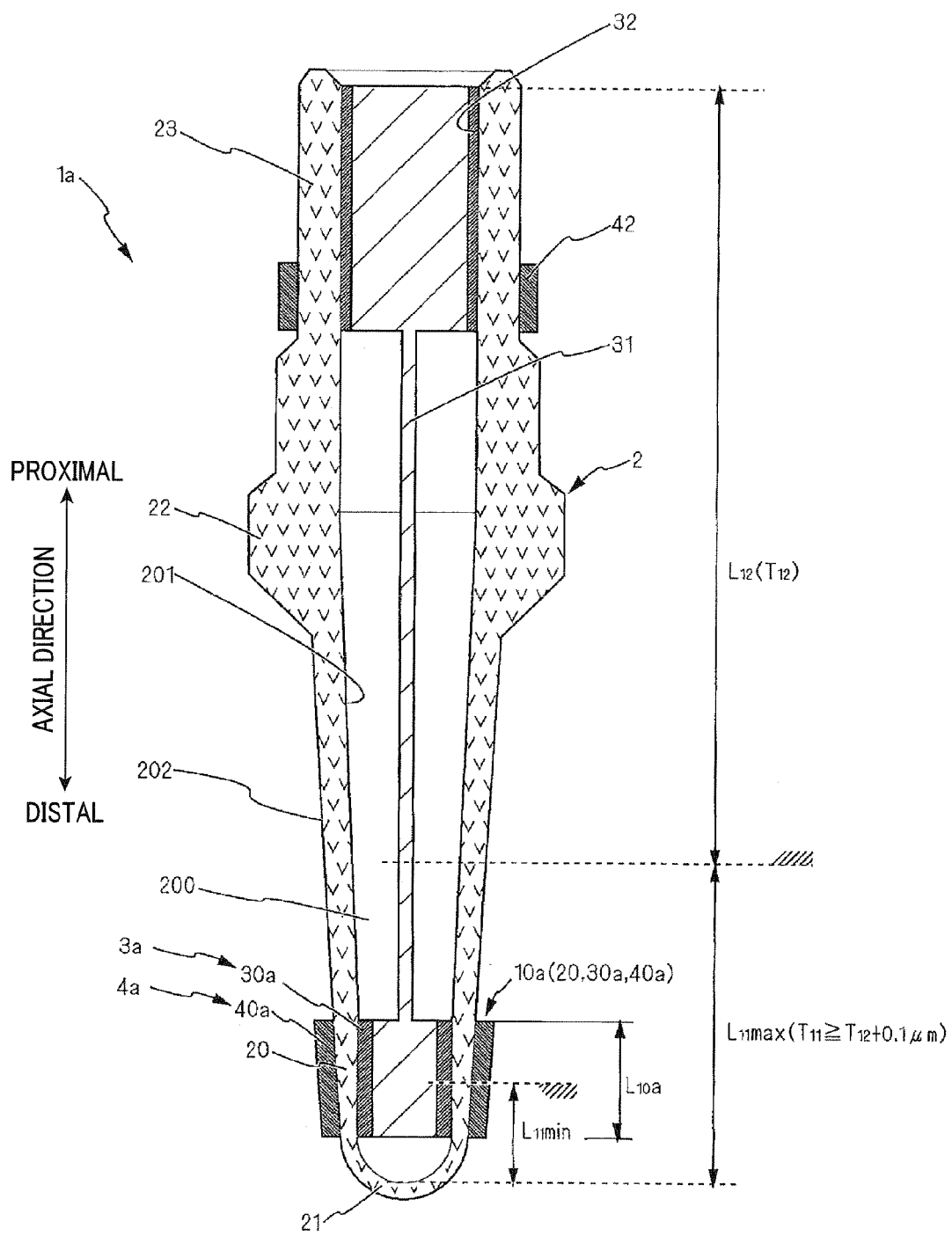
FIG. 14 is a longitudinal cross-sectional view of a gas sensor element according to a second embodiment.

Referring now to FIG. 14, a gas sensor element 1a according to a second embodiment will be described.

The gas sensor element 1a according to the second embodiment has almost the same structure as the gas sensor element 1 according to the first embodiment. Accordingly, only the differences therebetween will be described hereinafter.

In the first embodiment, the detection portion 30 of the reference electrode 3 is formed on the inner surface 201 of the solid electrolyte body 2 so as to extend from the distal end of the inner surface 201 proximalward. The detection portion 40 of the measurement electrode 4 is formed on the outer surface 202 of the solid electrolyte body 2 so as to extend from the distal end of the outer surface 202 proximalward. Consequently, the inner and outer surfaces of the bottom portion 21 of the solid electrolyte body 2 are respectively covered by the detection portion 30 of the reference electrode 3 and the detection portion 40 of the measurement electrode 4 (see FIG. 1).

In comparison, in the second embodiment, as shown in FIG. 14, the detection portion 30a of the reference electrode 3a and the detection portion 40a of the measurement electrode 4a are respectively formed on the inner and outer surfaces 201 and 202 of the solid electrolyte body 2 so that the bottom portion 21 of the solid electrolyte body 2 is exposed from both the detection portions 30a and 40a of the reference and measurement electrodes 3a and 4a.

In addition, in the second embodiment, the detection portion 10a of the gas sensor element 1a is comprised of the detection portion 30a of the reference electrode 3a, the detection portion 40a of the measurement electrode 4a, and that portion of the solid electrolyte body 2 which is interposed between the detection portions 30a and 40a of the reference and measurement electrodes 3a and 4a.

The gas sensor element 1a according to the second embodiment can be manufactured with the same method as the gas sensor element 1 according to the first embodiment.

In particular, in the base forming step P0, it is possible to use the porous support like a pen nib to apply the active base material only on that area of the inner surface 201 of the solid electrolyte body 2 where the reference electrode 3a is to be formed. Consequently, it is possible to form the detection portion 30a of the reference electrode 3a into the annular shape as shown in FIG. 14 without performing a masking process.

Moreover, in the second embodiment, it is also possible to form the reference electrode 3a to have a larger thickness $T_{11}$ in a large-thickness region $L_{11}$ and a smaller thickness $T_{12}$ in a small-thickness region $L_{12}$. Consequently, it is possible to achieve the same advantages as in the first embodiment. In particular, it is possible to reduce the amount of platinum used for formation of the reference electrode 3a while securing both high durability and stable output of the gas sensor element 1a.

While the above particular embodiments have been shown and described, it will be understood by those skilled in the art that various modifications, changes and improvements may be made without departing from the spirit of the present invention.

What is claimed is:

1. A gas sensor element comprising:
a cup-shaped solid electrolyte body having a closed end on a distal side and an open end on a proximal side in an axial direction of the solid electrolyte body;
a reference electrode provided on an inner surface of the solid electrolyte body; and
a measurement electrode provided on an outer surface of the solid electrolyte body,
wherein
the gas sensor element has a detection portion of a predetermined extent located closer to the closed end than to the open end of the solid electrolyte body,
the detection portion of the gas sensor element is comprised of a detection portion of the measurement electrode to be exposed to a measurement gas, a detection portion of the reference electrode to be exposed to a reference gas, and a portion of the solid electrolyte body interposed between the detection portions of the measurement and reference electrodes,
the measurement electrode further has a terminal portion located closer to the open end than to the closed end of the solid electrode body and a lead portion connecting the detection and terminal portions of the measurement electrode,
the reference electrode further has a terminal portion located closer to the open end than to the closed end of the solid electrode body and a lead portion connecting the detection and terminal portions of the reference electrode, the reference electrode has a first thickness in a large-thickness region and a second thickness smaller than the first thickness in a small-thickness region, wherein the reference electrode includes a step change in thickness from the large thickness region to the small thickness region, the large-thickness region includes at least part of the detection portion of the reference electrode, and the small-thickness region includes at least the lead and terminal portions of the reference electrode, a proximal end of the large-thickness region is positioned in the axial direction of the solid electrolyte body within a range of 5 to 20 mm from a distal end of the inner surface of the solid electrolyte body, and the lead portion of the reference electrode is formed over only part of a circumference of the inner surface of the solid electrolyte body.

2. The gas sensor element as set forth in claim 1, wherein the large-thickness region includes at least a region in which when the gas sensor element is heated by a heater to activate the solid electrolyte body, the temperature of the reference electrode is within a range of 1.5% from a maximum temperature of the detection portion of the reference electrode.

3. The gas sensor element as set forth in claim 1, wherein the detection portion of the reference electrode is formed over an entire circumference of the inner surface of the solid electrolyte body, the lead portion of the reference electrode is formed in the shape of a strip extending in the axial direction of the solid electrolyte body at a constant circumferential width, and the terminal portion of the reference electrode is formed over an entire or partial circumference of the inner surface of the solid electrolyte body.

4. The gas sensor element as set forth in claim 1, wherein the first thickness of the reference electrode in the large-thickness region is larger than the second thickness of the reference electrode in the small-thickness region by 0.1 μm or more.

5. The gas sensor element as set forth in claim 1, wherein the first thickness of the reference electrode in the large-thickness region is greater than or equal to 0.6 μm and less than or equal to 1.4 μm.

6. The gas sensor element as set forth in claim 1, wherein part of the detection portion of the reference electrode falls outside the large-thickness region, and the part of the detection portion of the reference electrode has the second thickness which is greater than or equal to 0.5 μm and less than or equal to 1.4 μm.

7. The gas sensor element as set forth in claim 1, wherein both the lead and terminal portions of the reference electrode have the second thickness which is greater than or equal to 0.5 μm and less than or equal to 1.4 μm.

8. The gas sensor element as set forth in claim 1, wherein the lead portion of the reference electrode has a circumferential width less than or equal to 9 mm.

9. The gas sensor element as set forth in claim 1, wherein the entire measurement electrode has a constant thickness which is greater than or equal to 0.7 μm and less than or equal to 1.8 μm.

10. A gas sensor comprising:
the gas sensor element as set forth in claim 1;
a heater that is arranged inside the solid electrolyte body of the gas sensor element and generates heat upon being supplied with electric power;
a first signal wire for external connection of the gas sensor;
a first connector that connects the terminal portion of the reference electrode of the gas sensor element to the first signal wire and holds the heater;
a second signal wire for external connection of the gas sensor;
a second connector that connects the terminal portion of the measurement electrode of the gas sensor element to the second signal wire;
a pair of power supply wires for supplying electric power to the heater;
a pair of third connectors that respectively connect the pair of power supply wires to the heater;
a tubular housing that receives and holds the solid electrolyte body of the gas sensor element therein;
an insulator that insulates and holds the first connector, the second connector and the pair of third connectors;
a tubular casing that covers a proximal end portion of the gas sensor element, bundles the first signal wire, the second signal wire and the pair of power supply wires together and hermetically seals those wires; and
a cover that covers and thereby protects the detection portion of the gas sensor element which protrudes from a distal end of the housing.

11. A method of manufacturing the gas sensor element as set forth in claim 1, the method comprising a base forming step, a first plating step and a second plating step, wherein in the base forming step, an active base material, which contains an organic platinum complex and a volatile solvent, is applied on a predetermined area of the inner surface of the solid electrolyte body and heat-treated to deposit platinum nuclei on the predetermined area where the reference electrode is to be formed, in the first plating step, a plating solution and a reducing agent are filled into an internal space of the solid electrolyte body so as to immerse only that part of the active base material which is applied on an area of the inner surface of the solid electrolyte body where the large-thickness region is to be formed, thereby depositing platinum only on the area of the inner surface, and in the second plating step, a plating solution and a reducing agent are filled into the internal space of the solid electrode body to immerse all the active base material applied on the inner surface of the solid electrolyte body, thereby depositing platinum to form the reference electrode.

12. The method as set forth in claim 11, wherein the plating solution used in the second plating step has a lower concentration than the plating solution used in the first plating step.

13. The method as set forth in claim 11, wherein in the base forming step, the active base material is first impregnated into a porous support, which is formed of one of a porous rubber material, a sponge material, a felt material and a fibrous ceramic compact, and then applied on the predetermined area of the inner surface of the solid electrolyte body using the porous support.

14. The method as set forth in claim 11, wherein the volatile solvent contained in the active base material has a boiling point lower than or equal to 108° C.

* * * * *